United States Patent [19]

Cheu et al.

[11] Patent Number: 5,051,931

[45] Date of Patent: Sep. 24, 1991

[54] METHOD AND APPARATUS FOR EXERCISING THE EYES

[75] Inventors: Richard A. Cheu, Fair Haven, N.J.; Joel A. Dancyger, New York; Glenn A. Seifert, South Hampton, both of N.Y.

[73] Assignee: DynaVision, Inc., Red Bank, N.J.

[21] Appl. No.: 384,818

[22] Filed: Jul. 25, 1989

[51] Int. Cl.[5] .............................................. A61B 13/00

[52] U.S. Cl. ................................ 364/550; 128/25 A; 128/745

[58] Field of Search ................... 364/550, 551.01, 525; 340/825.19, 706; 128/25 A, 76.5, 676, 745, 793; 350/418; 351/203, 243, 244

[56] References Cited

U.S. PATENT DOCUMENTS

| | | | |
|---|---|---|---|
| 2,445,519 | 7/1948 | Floegel | 351/203 |
| 2,718,227 | 9/1955 | Powell | 351/203 |
| 2,735,423 | 2/1956 | Powell | 351/203 |
| 2,840,073 | 6/1958 | Zeltzer et al. | 351/203 |
| 3,460,530 | 8/1969 | Lorenz | 351/203 |
| 3,545,847 | 12/1970 | Pietrini | 351/203 X |
| 4,756,305 | 7/1988 | Mateik et al. | 128/76.5 |
| 4,824,237 | 4/1989 | Ratner | 351/203 |
| 4,838,677 | 6/1989 | Bronskill et al. | 351/203 |

*Primary Examiner*—Joseph L. Dixon

*Attorney, Agent, or Firm*—Myers, Rose & Liniak

[57] ABSTRACT

A method and apparatus for progressive user interactive exercise of the eyes, utilizing a computer connected to a computer display terminal having a screen, featuring Eye Movement, Fusion and Focusing Exercises and Apparatus that can be used separately or as a single unit. The Eye Movement and Fusion Exercises and Apparatus, therefore, have the option of giving the user a quantitative result indicating the user's level of accomplishment. The Eye Movement and Fusion Exercises offer a range of progressively more difficult choices. The quantitative results can be weighed to give a higher or lower score, depending upon the level of difficulty chosen for an exercise, and can also be cross-referenced with other responses to form reports.

34 Claims, 27 Drawing Sheets

Microfiche Appendix Included
(58 Microfiche, 1 Pages)

2210

METHOD AND APPARATUS FOR EXERCISING THE EYES

REFERENCE TO MICROFICHE APPENDIX

A microfiche appendix of one microfiche and fiftyeight total frames, containing the computer source program listings of the exemplary computer programs described in this Application, has been submitted as part of this Application and is incorporated herein by reference. The program consists of the program modules V, V1, V2, V3, V4, V5, V6, V7, V8, V9, V10, V11, V12, V13, V14, V15, V16, REPORT.1, REPORT.2, and REPORT.3. The titles of the modules contained in the program listing correspond to those referenced in the flow diagrams and the Detailed Description of the Invention.

BACKGROUND OF THE INVENTION

The present invention relates to a method and apparatus of exercising the eyes. More particularly, this invention relates to a progressive and interactive method and apparatus of exercising the eyes and relieving eye stress and strain resulting from extended viewing video display terminals (VDT).

The United States economy, as well as that of many other foreign countries, has moved from an industrial era to a service era and has now entered the information age. The computer has become the common denominator for providing services and information in today's workforce. Based on data from the American Optometric Association, 44 million workers in the United States interact with a computer in the course of their daily work activities. It is estimated that 15 million workers in the United States work with a computer extensively each day and would be classified as VDT operators. It is predicted that this number will rise to 28 million by 1993. These statistics are even more overwhelming when coupled with the dramatic rise in the number of people who continue to use personal computers at home, after work hours.

This explosive growth in the use of computers, and the resultant benefits they bring in all segments of the economy, has not been without problems. The eyes are the gateway to the mind and body, which makes VDT work possible. However, demands on the visual system, in the form of use of VDTs has placed VDT users in a very precarious position. Increased usage of the VDTs means greater demands on the visual system.

A large proportion of people who work with a computer on a regular basis experience some form of stress and/or physical discomfort of the eyes, as a result of that use. Some of these problems are not caused by the eye itself, but stress and fatigue of the muscles that control the eye. These problems are further magnified by the fact that difficulties in seeing and focusing generally increase with the age of the user. Although stress and fatigue of the eye muscles is common among regular VDT users, similar eye problems can be seen in many other occupations or activities that largely depend upon the eyes. Eye muscle problems can affect the users in many ways, some of which include deterioration of visual abilities, decreased productivity, increased employee turnover, and health insurance claims.

To prevent a deterioration in visual capabilities, the ocular muscles must be able to adapt to do the increased demands posed by long-term use of VDT. This requires a physiological improvement to provide the necessary level of adaptation to the muscular task. Vision is a neuro-muscular action that responds to the stimulus of light. Vision is a learned skill that can be trained to improve control. Three visual skills have been identified as being important to VDT usage. These three skills are: fusion (ability of the eyes to work together as a unit; accommodation (ability of the eyes to focus near, then far, without experiencing blurred vision); and saccadic movement (ability of the eyes to move accurately and rapidly). Eye movement is controlled by six muscles in each eye, and like all trainable muscles, when properly trained, produce efficient results. Likewise, when trainable eye muscles are "out of shape or overworked", the same effect results as with any other muscle in the body: fatigue, strain, movement error and pain.

It is known that physical training imposes stress on the body tissues, in particular, the muscles. Regular muscular activity, which occurs during training, can be considered a positive form of stress because it stimulates growth and improves muscular performance. Most of the changes that occur in a muscle, as a result of training, are gradual and occur over several weeks or months. The magnitude of these muscular adaptations is somewhat proportional to the amount of exercise performed during training. Muscles will adapt optimally, however, to exercise that moderately exceeds its capacity, necessitating a gradual progression in training load in order to maximize muscle performance.

Attempts to address the problems of eye stress and fatigue, to this date, have involved devices to reduce glare of VDT screens, rest breaks for VDT users and prescription glasses. These solutions have only provided for after the fact symptomatic relief and have not attacked and attempted to lessen or eliminate the root causes of the problem muscle strain and fatigue. Known eye exercises to this date have been used primarily for diagnosing or testing for eye problems. Even relatively simple exercises have not been developed for many eye problems. Those that have been developed strictly as exercises to strengthen the eye muscles, have not offered a full range of necessary exercise, have been rather crude, have not offered progressive training, or have not offered quantitative measures of progress or ability related to the exercises. Furthermore, these exercises have not been capable of easily and inexpensively being integrated into a computer user's environment or providing immediate feedback to the individual user.

SUMMARY OF THE INVENTION

It is an object of this invention to provide a method and apparatus for progressive user interactive exercise of the eyes, utilizing a computer connected to a computer display screen, featuring Eye Movement, Fusion and Focusing Exercises that can be used separately or as a single unit.

It is a further object to provide a method of Eye Movement and Fusion Exercises and apparatus, therefore, that have the option of giving the user a quantitative result indicating the user's level of accomplishment in the exercises.

It is yet another object of the invention to provide a method and apparatus for offering a range of progressively more difficult choices for the Eye Movement and Fusion Exercises.

It is still another object of the invention to vary the quantitative result achieved on the exercise, depending upon the level of difficulty chosen for a given exercise.

It is still another object of the invention to provide a method and apparatus for collecting and analyzing user data from all users engaging in the exercises.

Yet another object of the invention is to provide a novel method and apparatus for computer displayed Eye Movement Exercise.

Yet another object of the invention is to provide a novel method and apparatus for computer displayed Fusion Exercise.

Yet another object of the invention is to provide a novel computer displayed Focusing Exercise.

These and other objects are satisfied by a method and apparatus for progressive user interactive exercise of the eyes, utilizing a computer connected to a computer display screen, featuring Eye Movement, Fusion and Focusing Exercises that can be used separately or as a single unit.

DETAILED DESCRIPTION OF THE INVENTION

Figure 1:
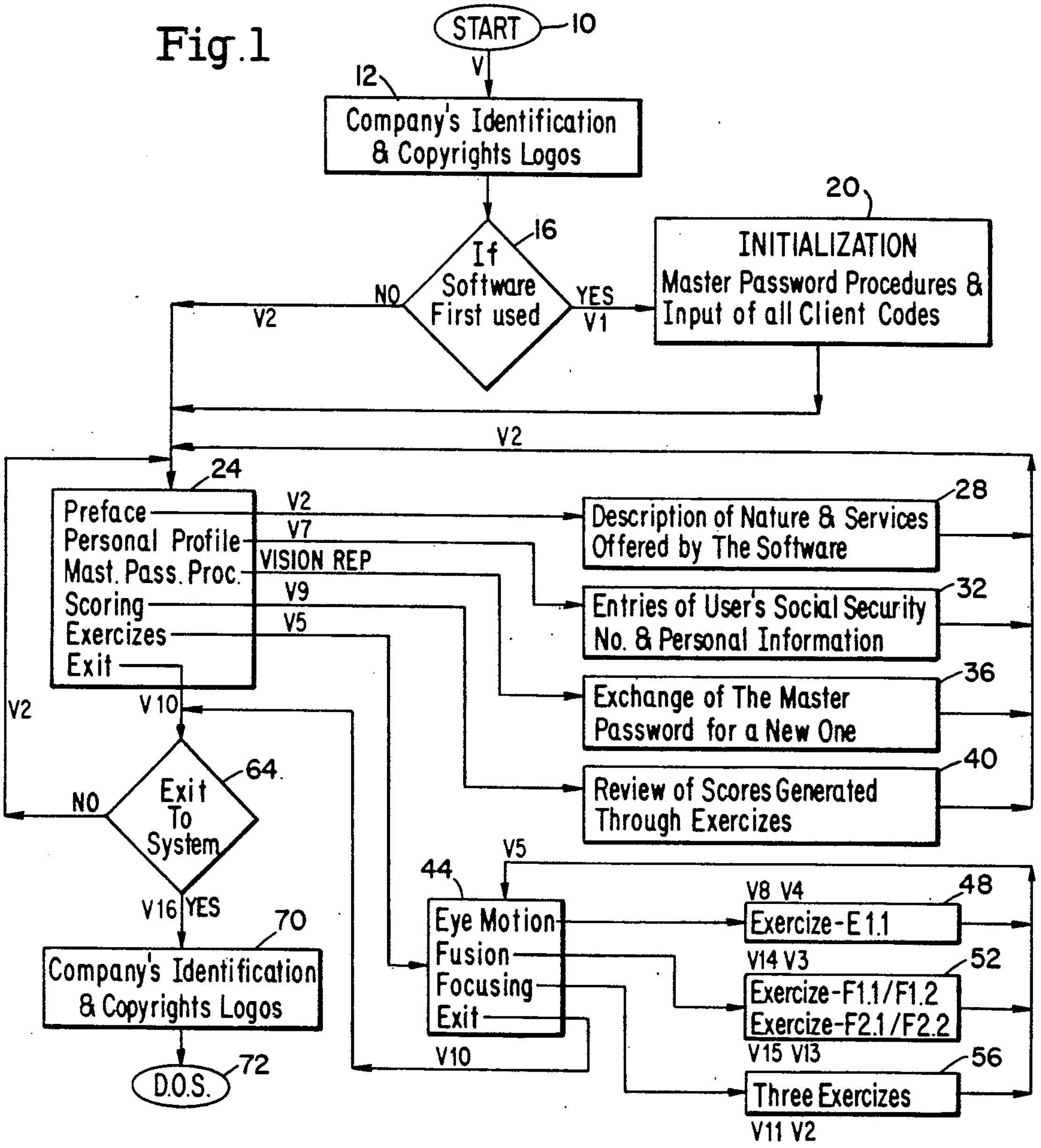
FIG. 1 illustrates the overall flow diagram for the computer programs, according to the present invention.

Referring now specifically to FIG. 1 of the accompanying drawing, the method of the present invention is illustrated in block diagram format. Program modules identified in the blocks perform most of the major steps of the method. Other steps are performed by the operator. The compilation of all program modules of the present invention is hereinafter referred to as VISION AEROBICS.

The general flow interaction of the programs of the present invention is illustrated in FIG. 1. It should be understood that the vision exercises of the present invention could also be performed without the aid of a computer, or manually. However, the best mode contemplated by the inventor is to provide them in a progressive and interactive computer software package that stores quantitative results from the exercises for further personal or statistical analysis. As can readily be appreciated by one skilled in the art, the code of the computer programs of the present invention could also be embedded in a semi-conductor chip or hardwired into a computer system, and this is also contemplated by the present invention. The software package of the present invention is designed to be used by a VDT operator as part of their everyday routine without having to leave their work station, or requiring any modifications of their VDT.

The VISION AEROBICS program will now be described in general terms, as illustrated in FIG. 1, before moving to a more detailed analysis. The user begins the visual exercise session in blocks 10 and 12, moving from the computer operating system to the execution file V by typing in that file name. After displaying the company's identification and intellectual property notices in block 12, the program identifies in block 16 whether or not the software has been used before. After the appropriate entries of identification numbers, client code and personal data, the main menu is displayed in block 24. The Main Menu allows the user to access all of the major program functions, including the description of the software (block 28), development of a personal profile (block 32), changing of the Master Password (block 36), a review of previous scores (block 40), access to the Eye Exercises (block 44), or exiting the program back to the operating system (block 64).

If the user choses to access the Eye Exercises in block 24, he must then specify his choice of exercise in block 44, and execute the chosen exercise in blocks 48, 52 or 56. The results are recorded upon completion of the interactive exercise, the user is then returned to the exercise menu of block 44. The Eye Motion, Fusion and Focusing exercises are separate and distinct, and the user can access one or more of the exercises without having to use the others. It has been found, however, that optimal results are generally achieved when approximately three minutes each of eye motion, fusion and focusing exercise per day are done using the present invention.

Figure 2:
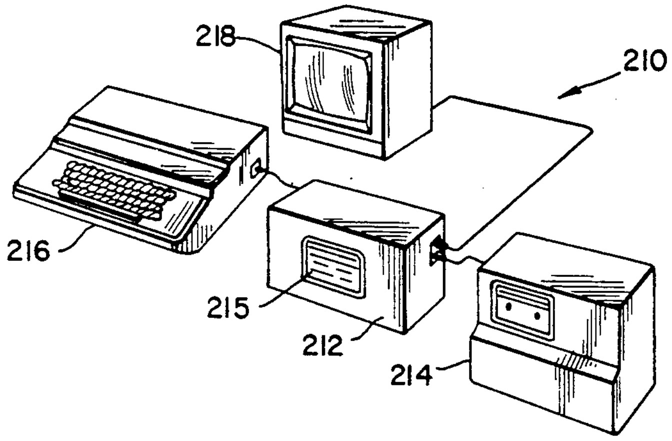
FIG. 2 illustrates representative hardware on which the computer programs of the present invention can be run.

Referring now to FIG. 2, there is illustrated exemplary computer hardware 210 on which the programs of the present invention can be run to perform the abovedescribed method. The VISION AEROBICS programs can be stored on a floppy disk to be inserted in disk drive 215, or on a hard disk or semi-conductor chip in computer 212 or mainframe system 214, connected to a computer 212. All of the memory devices produce, in conjunction with computer 212, the VISION AEROBICS programs on video display screen 218, which is connected to computer 212. The user interacts and enters responses to requests displayed on screen 218, utilizing keyboard 216.

An exemplary computer system employed for processing the VISION AEROBICS programs utilizes a Compaq 286, or similar compatible system, having at least five megabytes of ROM and 640K RAM. The computer preferably must have a 16-bit processor, such as an 80286 or similar compatible chip. The programs can be run, utilizing an 8-bit CPU chip, with a resultant reduction in speed. The computer must at least contain an EGA graphics card. The system discussed uses a standard operating system (DOS 3.0 or higher) connected to a downward compatible VGA terminal, such as a PRINCETON Graphic Systems ULTRASYNC, or similar monitor. The compiler is Microsoft Quick BASIC. As can readily be appreciated by one skilled in the art, the programs of the present invention could be written in different computer languages. Also, although described here in connection with a personal computer, it is also contemplated that the present invention could also easily be incorporated into a specialized portable device or a main frame computer system.

Leaving the hardware discussion for now and returning to a more detailed discussion of the program modules, whose general flow interaction is illustrated in FIG. 1 and discussed above, described in detail below are the logical flow pattern and interrelationships of the following programs designated as follows: V, V1, V2, V3, V4, V5, V6, V7, V8, V9, V10, V11, V12, V13, V14, V15 and V16. The actual program listings are supplied in the form of a microfiche appendix to this specification.

ACCESSING AND INITIALIZATION

Figure 3:
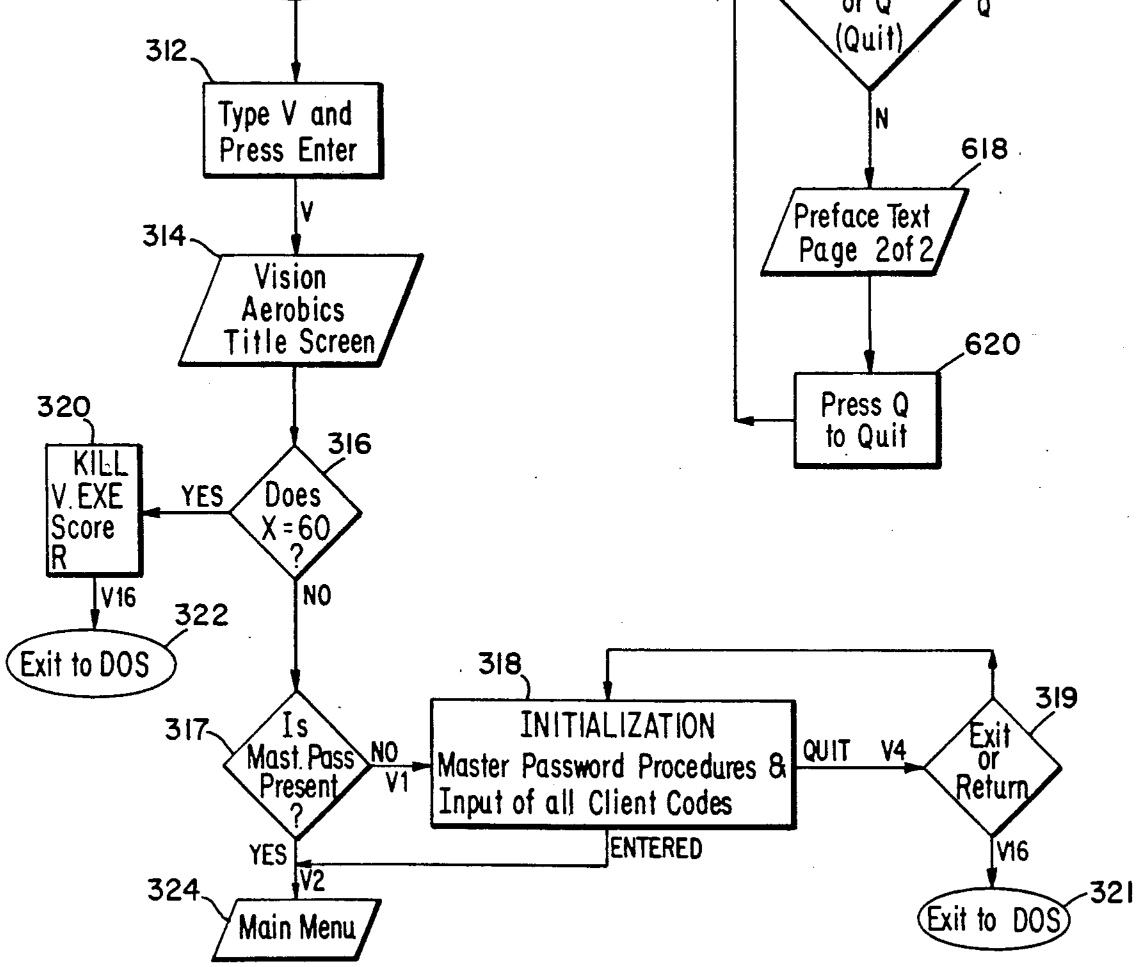
FIG. 3 illustrates the flow diagram for the Accessing and Initialization programs.
Figure 4:
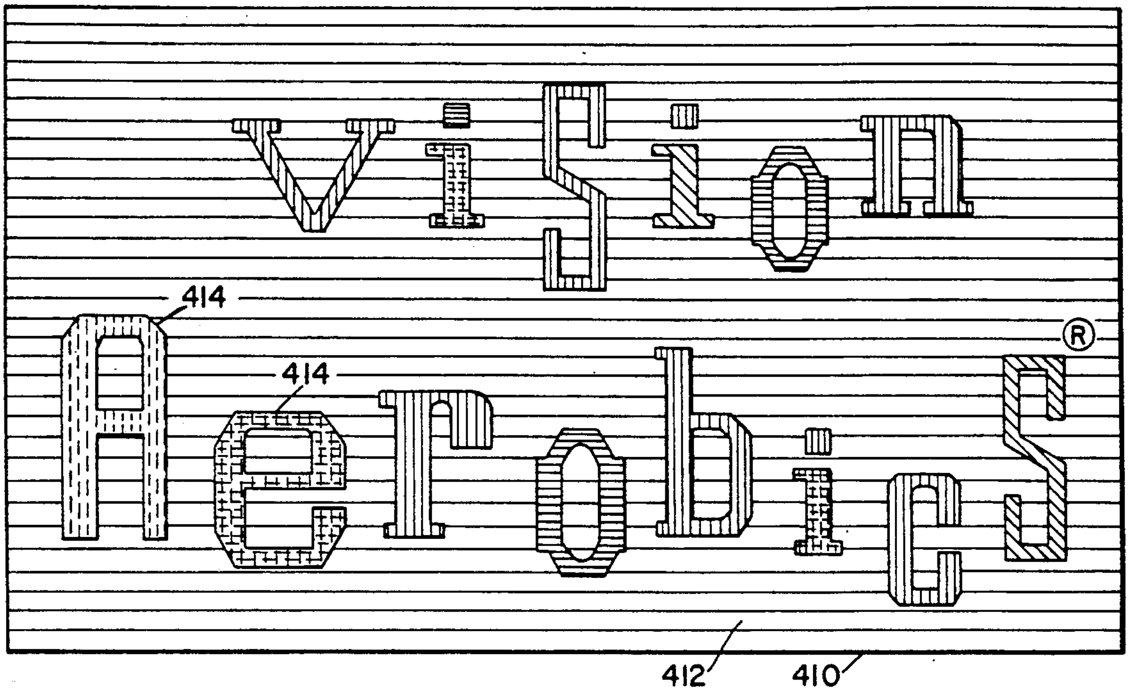
FIGS. 4 and 4A illustrate the title screen generated by the accessing program module V.
Figure 4A:
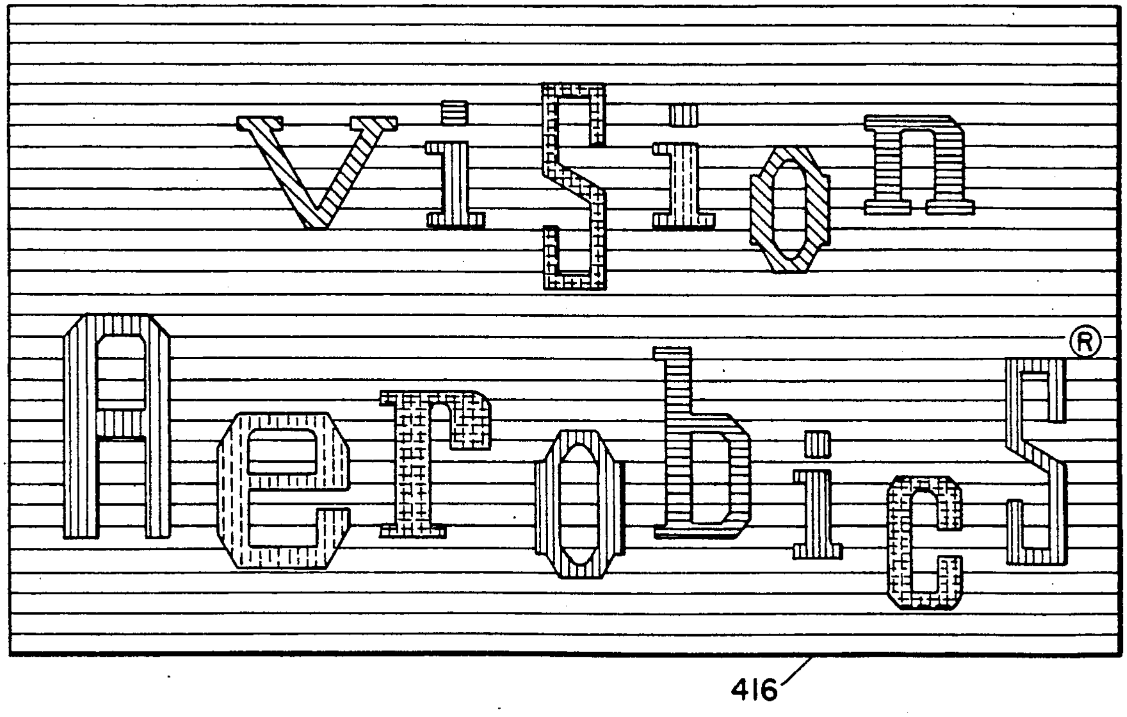

As previously described, with reference to FIG. 1, the V program is accessed by first entering the computer's operating system, then typing in the file name "V" and pressing Enter. The flow of this program is illustrated in more detail in blocks 310 and 312 of FIG. 3. Once the V program is accessed, it first produces the VISION AEROBICS title screen illustrated in block 314. That screen, 410, is illustrated in FIGS. 4 and 4A. Screens 410 and 416 are created by the program by first coloring the background 412, then forming the outlines of the letters 414, and then painting or filling the letters in with different colors. Accessing the title screen activates a timer that allows the image to display on the screen for 15 seconds. During that time, initial colors of each letter are continuously changed from left to right in the manner shown in FIGS. 4 and 4A, where the initial color of the "V", for example, next becomes the color of the "I", then the color of the "S" and so on. The color change gives a flowing or flashing effect to the letters on the screen. The V program can be interrupted and advanced by hitting any key on the keyboard. The V program also prints appropriate intellectual property notices on the screen. It will also be appreciated that the title screen could be customized to contain pertinent information, logos, adjust the time the screen is displayed, or advertising of a client that has licensed or purchased the VISION AEROBICS software.

The V program contains some of the major security optional features of the VISION AEROBICS software. The V program sets up a variable designated as X, which is initialized to equal zero. That variable serves as a counter and is increased by one each time a user accesses the program. Each time the V program is accessed, it checks the value of X, as illustrated in block 316 of FIG. 3. A maximum value can be set for the variable X, corresponding to the maximum number of times a user is allowed to access the system.

If the value of X in block 316 is greater than the designated number of maximum runs of the V program, 60 in this case, the V program executes a security sub-program to disable the V program and, therefore, the entire VISION AEROBICS program from any future use. This security sub-program is totally optional and is useful in combating theft of the software, or, if it is desired, to control the maximum number of uses of the software. The security sub-program, illustrated in block 320, erases all previously recorded score, biographical and social security information of the user, as well as all V programs, so that the VISION AEROBICS program cannot be accessed. The V program then accesses the V16 program, as illustrated in block 322 and returns the user to the computer operating system.

Returning to block 316, if the value of X is not 60, then the V program checks in block 317 to see if a Master Password has previously been entered. If the V program cannot find a Master Password in block 317, which indicates that the software is being used for the first time, the V program then calls for and runs the program V1. The V1 program in block 318 requires the user to enter a Master Password, social security number and personal identification number (PIN). The V program also requires the entry of the company code, site code and function code of the user's employer. These numbers serve two important functions, the first being security, since the programs, other than the V and V2 programs of the VISION AEROBICS program, cannot be accessed without first entering the PIN. Secondly, the entry of the password, social security number and client codes establishes data files for scoring data regarding the exercises that can later be accessed by the user or by one analyzing data and results collected, using the REPORT or other programs.

The V1 program is only accessed once (when there is no master password on file) during the life of the software. Once the proper information is entered, the V1 program then calls for the program V2, illustrated in block 324, which produces the Main Menu for the VISION AEROBICS program. Similarly, if the V program detects that a Master Password has been previously entered, the V2 program is called for and the Main Menu is produced in block 324.

Every time the VISION AEROBICS program requests a response or input from the user, a timer is begun. That timer gives the user a pre-determined time interval, such as 30 seconds, to make an entry. This function is controlled by the program V4, which also is accessed in response to a user selection to quit the program, and is illustrated in block 319. As illustrated in block 319, once more than thirty seconds have elapsed, or a quit command has been entered, the V4 program then gives the user the option of returning to the Main Menu screen or exiting to the computer operating system in block 321, utilizing the V16 program (described later in detail).

THE MAIN MENU

Figure 6:
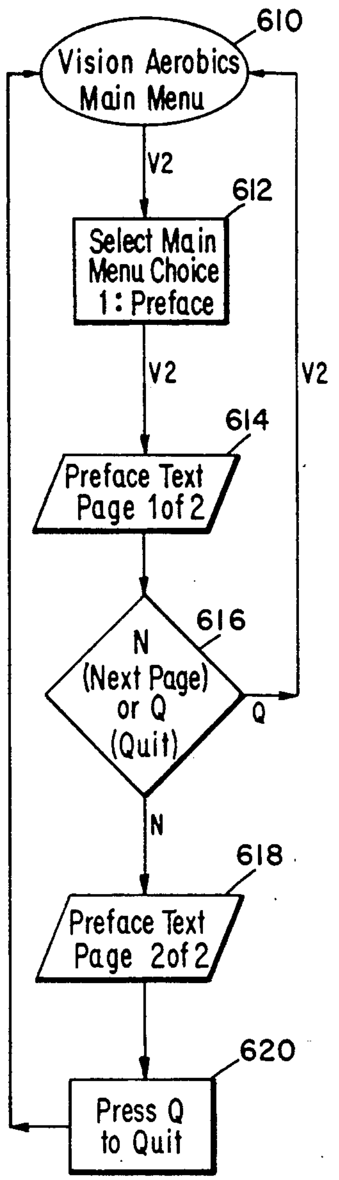
FIG. 6 illustrates the flow diagram for the Main Menu choice 1 Preface.
Figure 5:
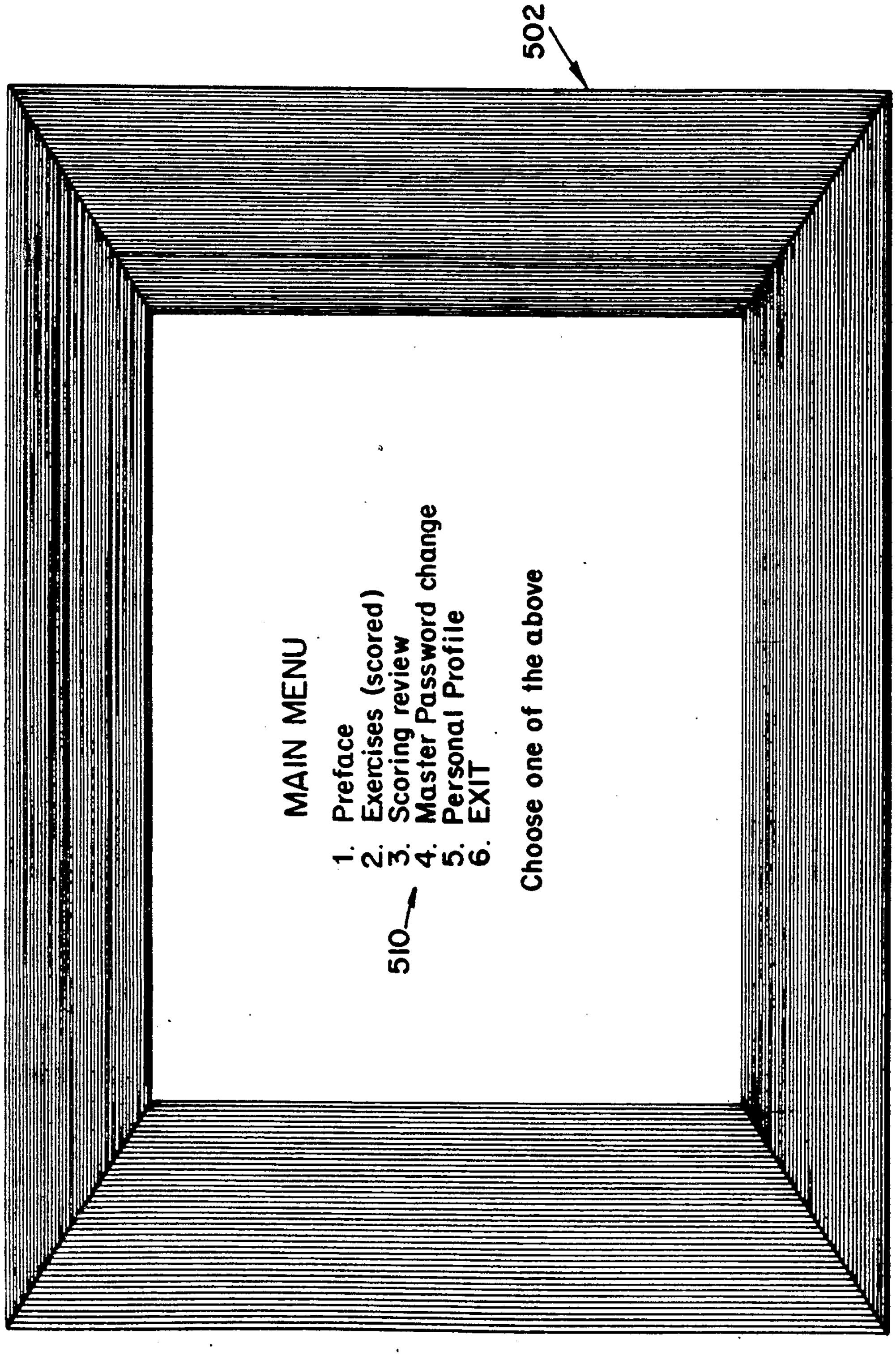
FIG. 5 illustrates the Main Menu computer screen display generated by the program V2.

The V2 program, illustrated in FIG. 1 by block 24, and in FIG. 6 by block 610, produces the VISION AEROBICS Main Menu. From this menu the user can select all of the major functions of the VISION AEROBICS program. The screen display 502 of the Main Menu is illustrated in FIG. 5. The Main Menu provides six potential choices as referred to generally as 510 in FIG. 5. We will now describe in more detail the program modules that are accessed by selecting one of the six options from the Main Menu.

MAIN MENU CHOICE 1 PREFACE

If the user selects choice 1 preface from the Main Menu, the V2 program module, as illustrated in FIG. 6, continues to run and displays on the screen a description of the nature and services offered by the software, illustrated in block 610. Once the first page of the preface text is displayed in block 614, the V2 program gives the user in block 616 the choice of displaying the next page of text in block 616 by entering N, or returning to the Main Menu in block 610 by entering Q. Once the preface is completely displayed, the V2 program returns the user to the Main Menu display illustrated in block 620.

MAIN MENU CHOICE 2 EXERCISES -(SCORED)

Figure 7:
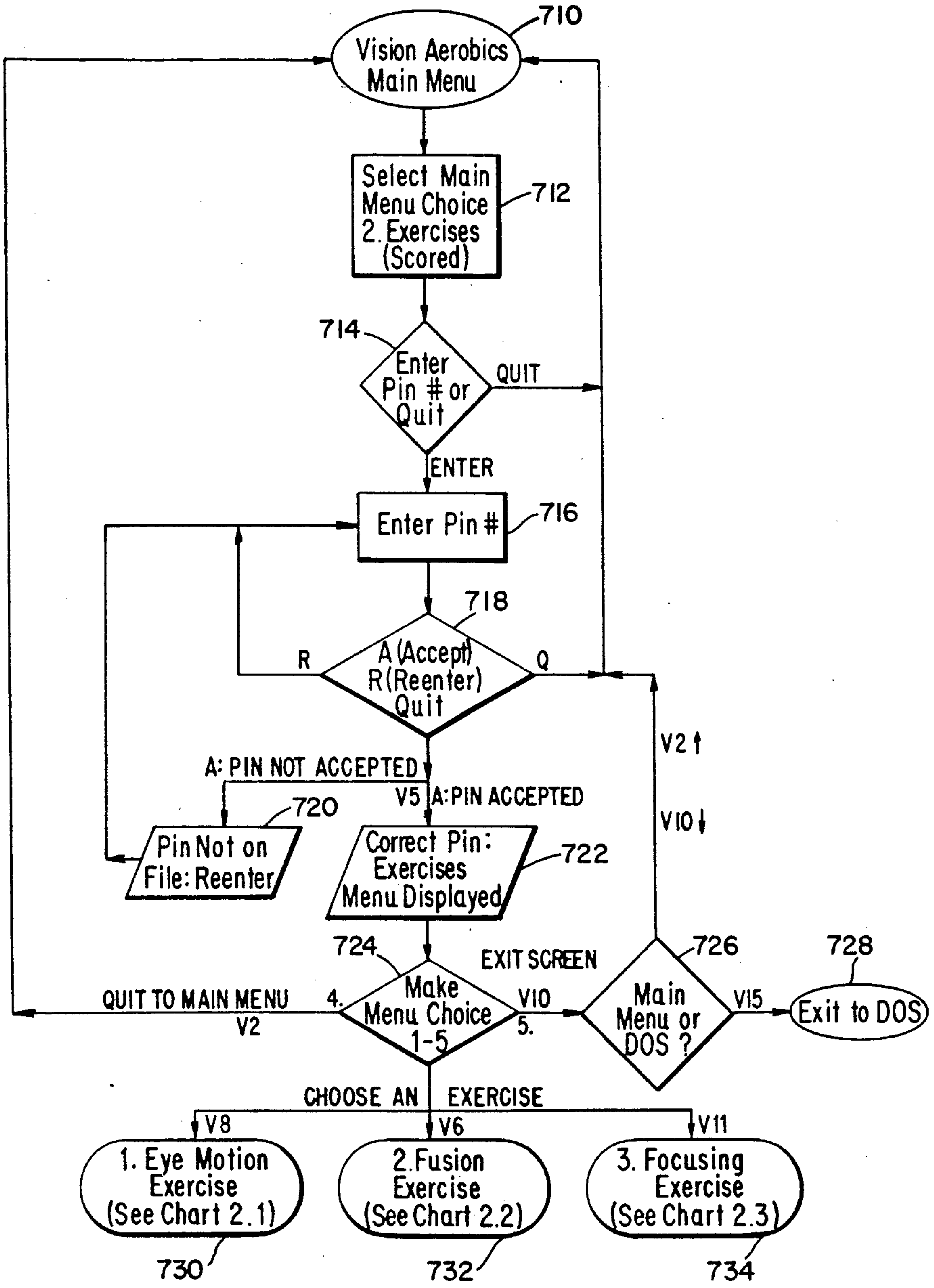
FIG. 7 illustrates the flow diagram for the Main Menu choice 2 Exercises (scored).

Turning now to FIG. 7, if Selection 2 Exercises (scored) is chosen from the main menu screen, illustrated in blocks 710 and 712, the V2 program calls for the user to enter his or her PIN number in block 716, or return to the Main Menu block 710 by entering Q. If a PIN number is entered, the V2 program in block 718 then requests the user to enter A to accept the PIN number and continue the program. If the correct PIN number is entered, the V2 program calls for and runs the V5 program. This program displays the Exercise Menu in block 722.

The menu of exercises is displayed on the screen by the program V5 in a similar format to that of the Main Menu, illustrated in FIG. 5. The Exercise Menu presents the user with five potential choices: 1. Eye Motion, 2. Fusion, 3. Focusing, 4. Go back to Main Menu, and 5. Exit.

If the user selects Choice 4 in block 724, the V5 program calls for the V2 program to return the user to the Main Menu. If the user selects Choice 5, the V5 program runs the V10 program, illustrated in block 726. The V10 program gives the user the choice of returning to the Main Menu, illustrated in block 710, by running the V2 program or exiting to the computer operating system, illustrated in block 728, by running the V16 program.

The remaining three choices, 1-3 of the Exercise Menu, form the heart of the present invention, the Eye Motion blocks Fusion and Focusing Exercises blocks 730, 732 and 734, respectively. As previously stated, these three types of exercises can be accessed and used independently. However, it is preferred that one of each of the types of exercises be done for approximately three minutes each per day. Choices 1-3 will now be discussed in detail in numerical order.

The Eye Movement Exercise (Choice 1) improves the ability of the eye muscles to make smooth, accurate, coordinated, more rapid, and therefore comfortable eye movements. This is done by directing the eye to be moved rapidly, in a smooth and coordinated manner, to condition the eye muscles which change the positioning of the eye.

Figure 8:
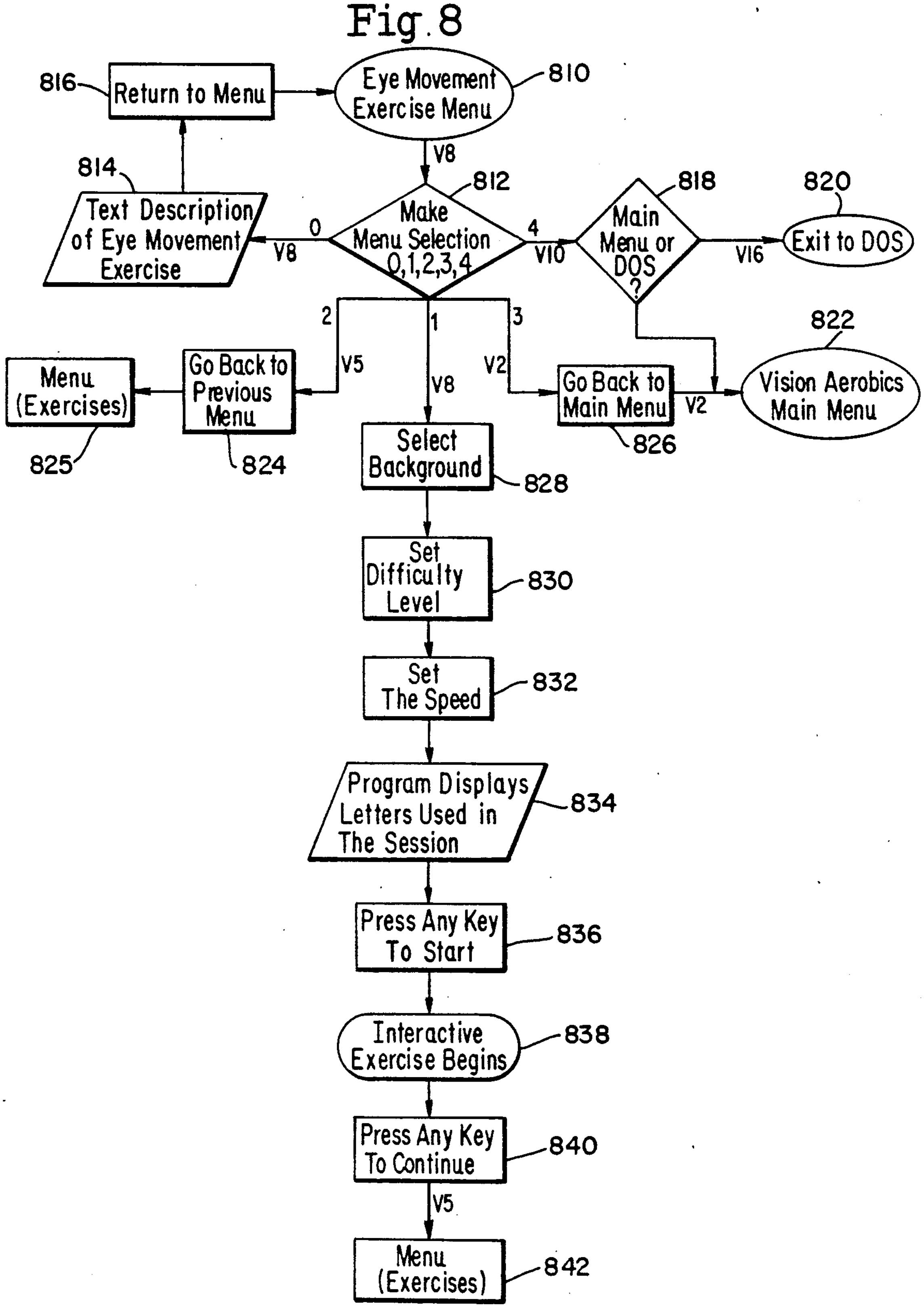
FIG. 8 illustrates the flow diagram for the Eye Motion Exercise programs.

The flow of the program modules that make up the Eye Motion Exercise is illustrated in detail in FIG. 8. The Eye Movement Exercise is designed to strengthen the muscles that physically move the eye from one viewing position to another. Once the user has made the eye movement selection from the Exercise Menu, the V8 program is run and displays the Eye Movement Exercise Menu, illustrated in block 810. The Eye Movement Exercise Menu is similar in format to the Main Menu produced by the V2 program, illustrated in FIG. 5. The Eye Movement Exercise Menu 810 offers five possible selections: 0. Description, 1. Exercise (E1.1), 2. Go back to previous menu, 3. Go back to Main Menu, and 4. Exit.

If the user selects Choice 0, the V8 program continues, and a text description of the Eye Movement Exercise is displayed in block 814. The screen displaying the text description in block 814 then instructs the user to press any key to continue. By depressing any key, the user moves to block 816, which returns him to the Eye Movement Exercise Menu, illustrated in block 810.

If the user selects Choice 4 Exit in block 812 from the Eye Movement Exercise Menu 810, the V10 program is run. The V10 program asks the user in block 818 to select either the Main Menu or the operating system. If the user selects the operating system, the V16 program is accessed, and he is exited to the computer operating system, as illustrated in block 820. If the user in block 818 selects the Main Menu, the V2 program is run, and the VISION AEROBICS Main Menu screen is produced, as illustrated in block 822.

Returning to block 812, if the user makes Menu Choice 2 from the Eye Movement Exercise Menu 810, the V5 program is run, as illustrated in block 824, and the Exercise Menu is displayed in block 825. Returning again to block 812, if the user selects Choice 3, the V2 program is run in block 826, and the user is returned to the VISION AEROBICS Main Menu in block 822.

If the user selects Choice 1 in block 812, the V8 program continues and the Eye Movement Exercise is initiated. The V8 program in blocks 828 through 832 produces selection screens illustrated generally as 900 in FIG. 9. The selection screen produces alternating letters L, K, A, and S, 910, 912, 914, and 916, respectively, in blocks arranged in parallel rows across the screen. The lower part of the screen contains a score indicator 918 and a time indicator 920. These two indicators tell the user his score and the elapsed time that he has been using the Eye Movement Exercise. Screen 900 also has a blank area 922, located just above the center of the screen.

Figure 9:
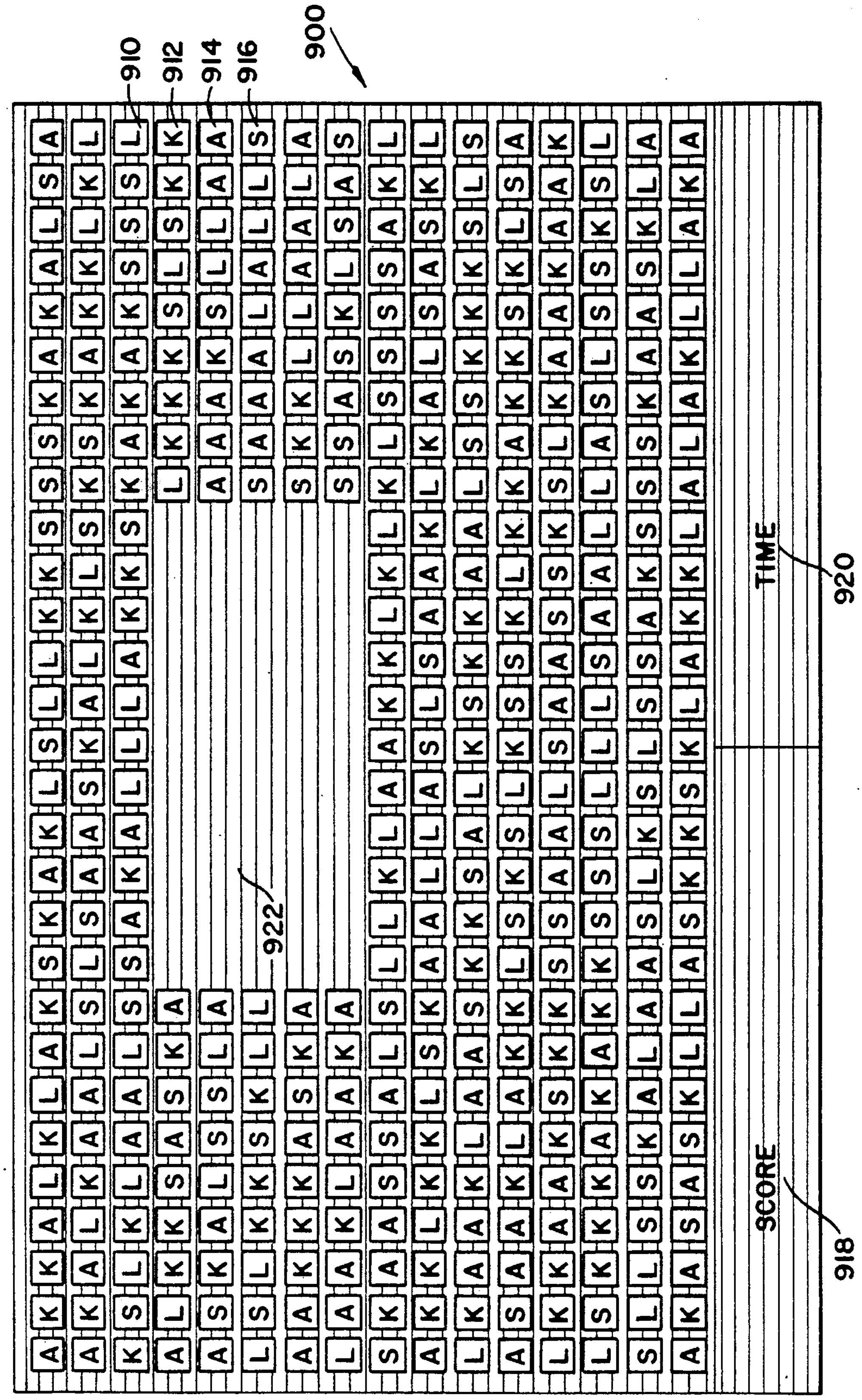
FIGS. 9–12 illustrate alternative screen displays generated by the Eye Motion Exercise programs.

Looking at FIG. 8 in conjunction with FIG. 9, the user is presented with a first screen in which he selects the background for the Eye Movement Exercise in block 828 of FIG. 8. Those choices are projected on the screen in the blank area 922 in FIG. 9, the choices for the background being: 1. Easiest, 2. Harder, 3. Hardest. Once the user has selected the background, the V8 program then moves to block 830 in FIG. 8, where the user is asked to to set the difficulty level. Another selection screen, such as that illustrated in 900 of FIG. 9, is presented. The choices of difficulty level are: 1. Lowest, in which case, two letters are used in the exercise; 2. Medium, in which case, three letters are used in the exercise; and 3. Highest, in which four letters are used in the exercise. Upon entering his choice, the user sees another V8 program selection screen 900, and the user is asked to set the speed of the Eye Movement Exercise, the choices being: 1. Lowest, 2. Medium, and 3. Highest.

The V8 program continues then to block 834, where it displays the letters that will be used in this session, which correspond to the selection made in block 830. The user is then prompted to press any key to start the exercise in block 836. By this time, the V8 program has already opened data files to collect the user's scores on the Eye Movement Exercises, recorded in combination with the user's personal data.

Figure 10:
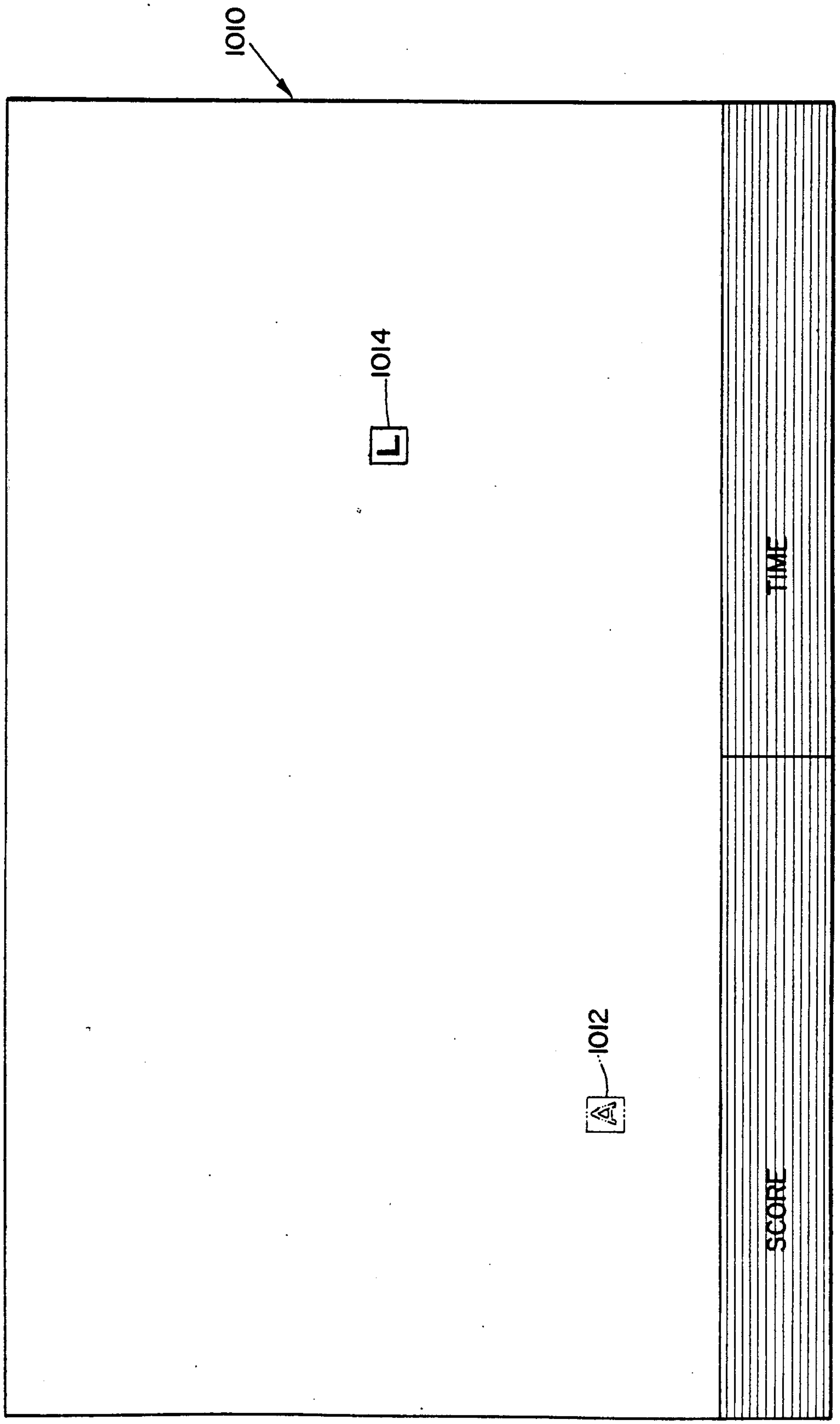
Figure 11:
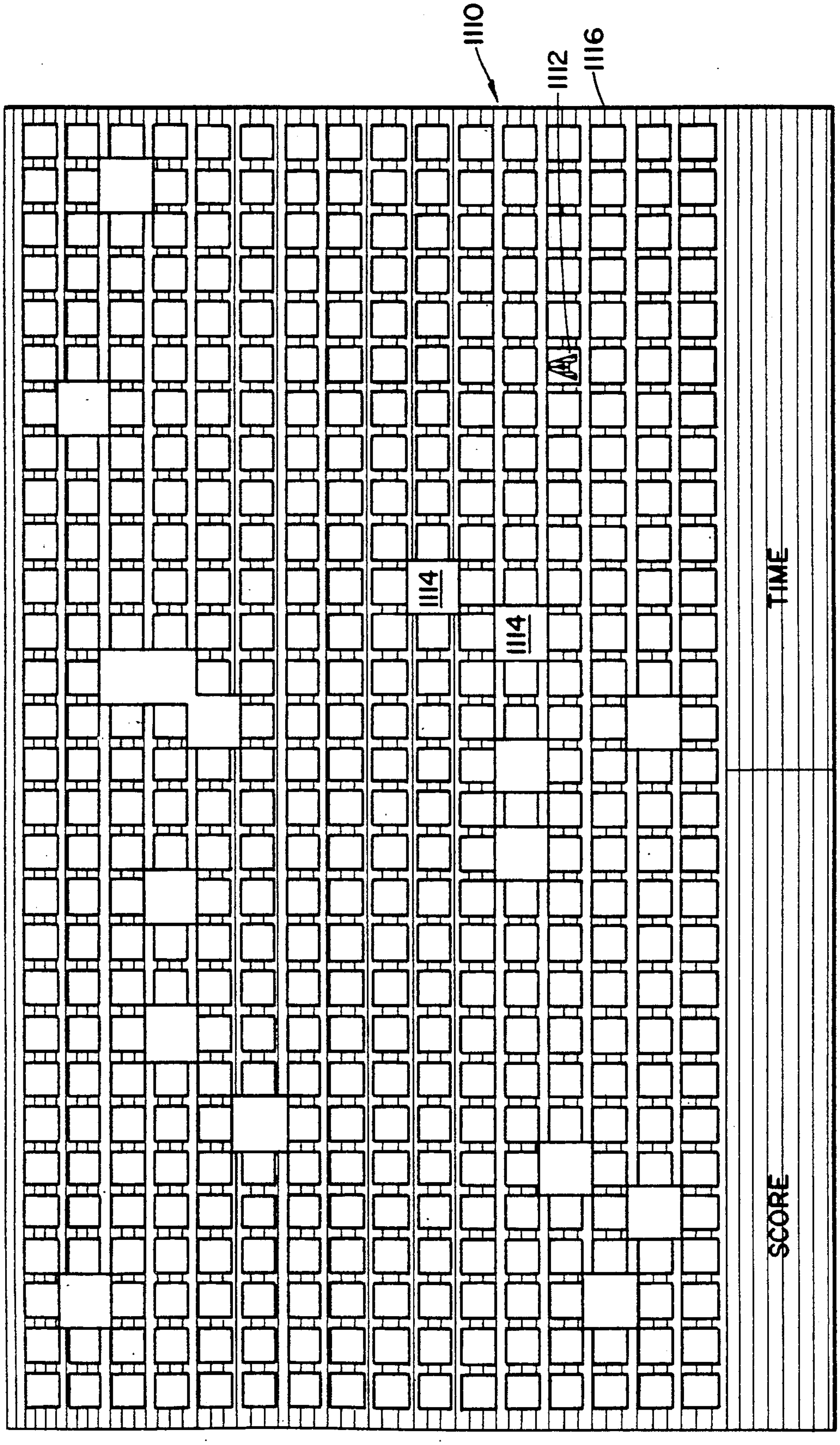
Figure 12:
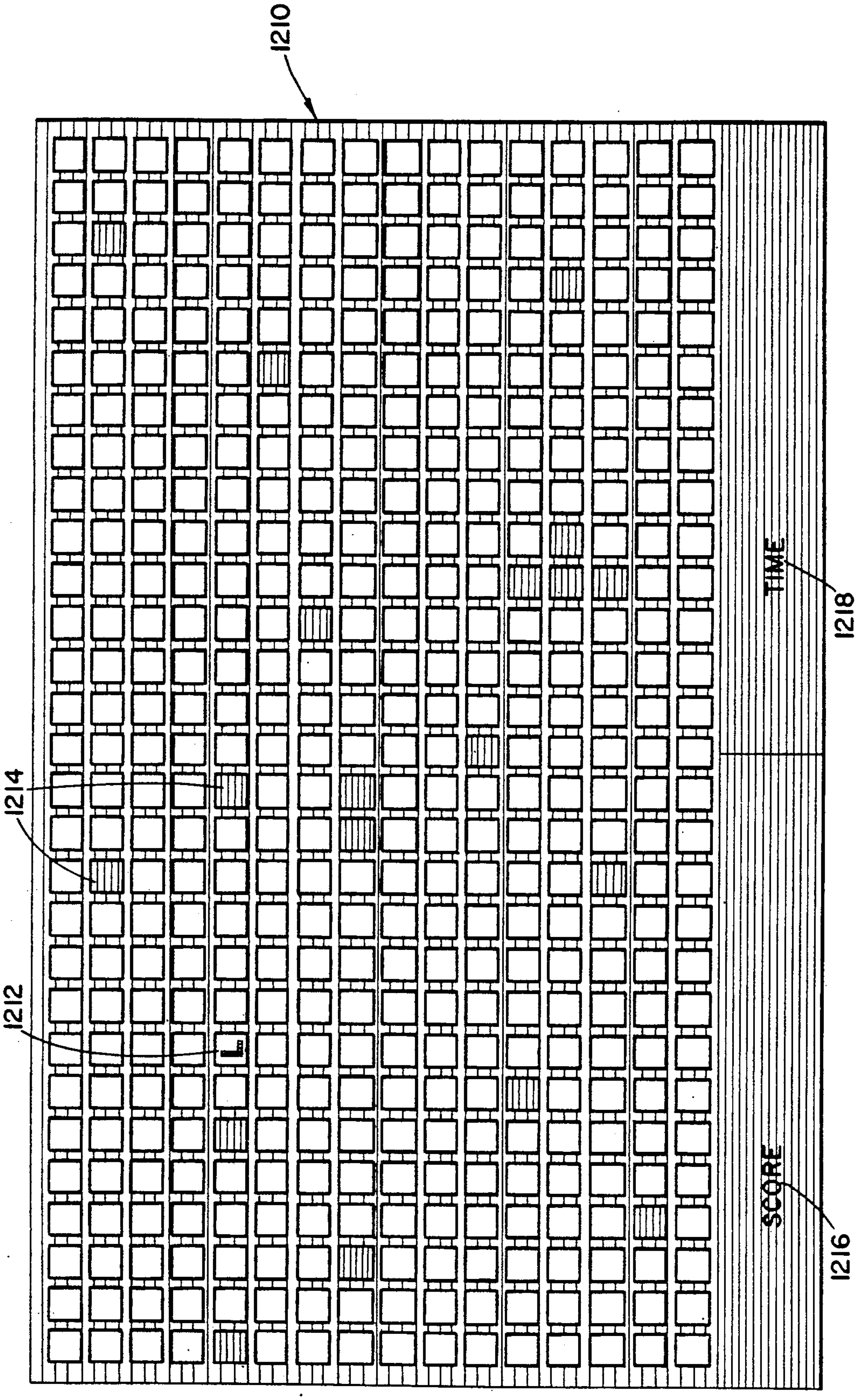

The Eye Movement Exercise of program module V8, as illustrated in FIGS. 10 through 12, is preferably a progressive user interactive three-minute timed exercise. The Eye Movement Exercise exercises the muscles that control movement of the eyes by projecting, at random, one of the selected letters at random locations on the screen, chosen from the number of possibilities selected in setting the difficulty level. The letters are displayed for a pre-selected time interval, depending upon the speed setting selected. The letter is then removed from the screen, and the user is given approximately two seconds to enter a correct response by striking the key that corresponds to the letter that was projected. If the user enters a correct response before the end of the two-second interval, the machine will then accelerate, and immediately project the next letter on the screen. The letters are successively projected, one at a time, at random locations throughout the screen. By making the user concentrate and move his eyes to the location of projection of each letter, in order to enter a correct response, the eye muscles are directed to make fluid movements around the screen at pre-selected intervals. This results in a progressive conditioning of the muscles that control movement of the eye.

As previously discussed, the Eye Motion Exercise contains three variables to make the exercise more or less demanding. The three variables are: the background against which the letters are projected, the number of different letters from which the selected letter is projected, and the speed at which the next letter will appear on the screen. This allows the user to progressively increase the load or requirements of the exercise as he is able to strengthen the muscles controlling his eye movement.

Addressing the variables in turn, it can be appreciated that as the speed is increased, it will require more eye movements in a given period of time, as the projection interval is is shortened. This results in a strengthening of the eye movement muscles, due to more repetitions over a given span of time. Likewise, the difficulty level or number of different letters that may appear, requires more concentration and more rapid movements. This occurs as the user is called upon to distinguish which of three or four letters is displayed in the medium and highest setting, rather than which of two letters in the lowest setting.

The difference in the background and how that relates to the Eye Movement Exercise can best be illustrated by referring to FIGS. 10 through 12. FIG. 10 illustrates the easiest background choice of the Eye Movement Exercise. Using this background screen referred to generally as 1010, a letter in a block 1012 is projected at a given location on the screen for a short interval of time. The letter 1012 then is removed, and the user has a short interval of time to record the proper letter that has appeared by striking the appropriate key on the computer keyboard. The program then randomly projects another letter 1014 in a block in another part of the screen, directing eye movement to another location, in order to identify the correct letter.

Moving now to FIG. 11, the screen display of the background Choice 2, Harder, is illustrated generally as 1110. The background of the "harder" choice is a grid of blocks arranged in parallel rows and columns overlaying a blue background. The Eye Movement Exercise, when used in conjunction with the harder background, projects a letter in a given block, illustrated as 1112. After the user has struck a key indicating which letter he believes it is, or has allowed a stated time interval to go by, the block, which had previously displayed the letter, is replaced by a white space shown as 1114.

Moving now to FIG. 12, Choice 3, the hardest background is illustrated generally as the screen 1210. Similar to FIG. 11, the display initially is composed of a series of white blocks arranged in rows and columns overlaying a blue background. Letter 1212 is again projected for a short interval of time, as shown, and then removed. The letter is then replaced in the blocks by a blue block, shown as 1214. As previously mentioned, the score 1216 and elapsed time 1218 are recorded at the bottom of the screen. The user scores points for every correct entry corresponding to a letter that has been projected on the screen and entered within a given time period after projection. The V8 program assigns a value of 1, 2 or 3 points to each variable chosen (difficulty in the background, speed or number of letters chosen). The score is obtained by multiplying the values of each variable together for each correct response.

It should be appreciated that the more difficult or distracting the background used in the Eye Movement Exercise when the letters are projected, the more concentrated and quicker the movement of the eyes must be to find and ascertain which letter is being projected. In this manner, the Eye Movement Exercise is not only an interactive, but also a progressive, muscular training tool which can accommodate large degrees of difference in eye movement muscle strength and ability. It has been found that the optimum time to engage in the Eye Movement Exercise is approximately three minutes per day. The V8 program records the quantitative score that the user attains in the Eye Movement Exercise, and enters that score, into a data file, and later cross-references it with the user biographical information, such as the user's social security number. Once the exercise is finished, the data file is closed. Returning to the flow diagram in FIG. 8, the V8 program then requests the user to press any key to continue in block 840. Once a key is struck, the V5 program is run, and the menu of exercises is displayed in block 842.

Moving now to the second progressive and interactive exercise of the VISION AEROBICS program, referring to FIG. 7, the Fusion Exercise and the program V6 are accessed by making Choice 2 from the Exercise Menu shown in block 732. Moving now to FIG. 13, the flow of the Fusion Exercise is illustrated. The V6 program first displays the Fusion Exercise Menu, illustrated in blocks 1310 and 1312 of FIG. 13, and requires the user to make one of six selections.

If the user makes the selection 0 in block 1312, the V6 program displays a single page of text describing the Fusion Exercise, and returns to the Exercise Menu in blocks 1316 and 1310. Similar to the Eye Movement Exercise, if the menu selection 5, Exit, is made, the V10 program is run, which asks in block 1318 whether the user would like to exit to the Main Menu or return to the computer operating system. If the user chooses to exit to the computer operating system, the V16 program is run, and the user is exited to the operating system in block 1320. If the Main Menu is chosen in block 1318, the V2 program is run, and the user is returned to the VISION AEROBICS Main Menu in block 1326. If menu selection 3 is made in block 1312, the V5 program is run, and the user is returned in block 1322 to the Fusion Exercise Menu of block 1310. If menu selection 4 is made in block 1312, the V2 program is run, and the user is returned to the VISION AEROBICS Main Menu in blocks 1324 and 1326. If the user makes menu selection 1 or 2 in block 1328 from the menu in block 1312, Fusion Exercises F1.1 and F1.2 are initiated, and program V3 is run. If option 2 is chosen, Fusion Exercises F2.1 and 2.2 are selected and program V13 is run.

Figure 13:
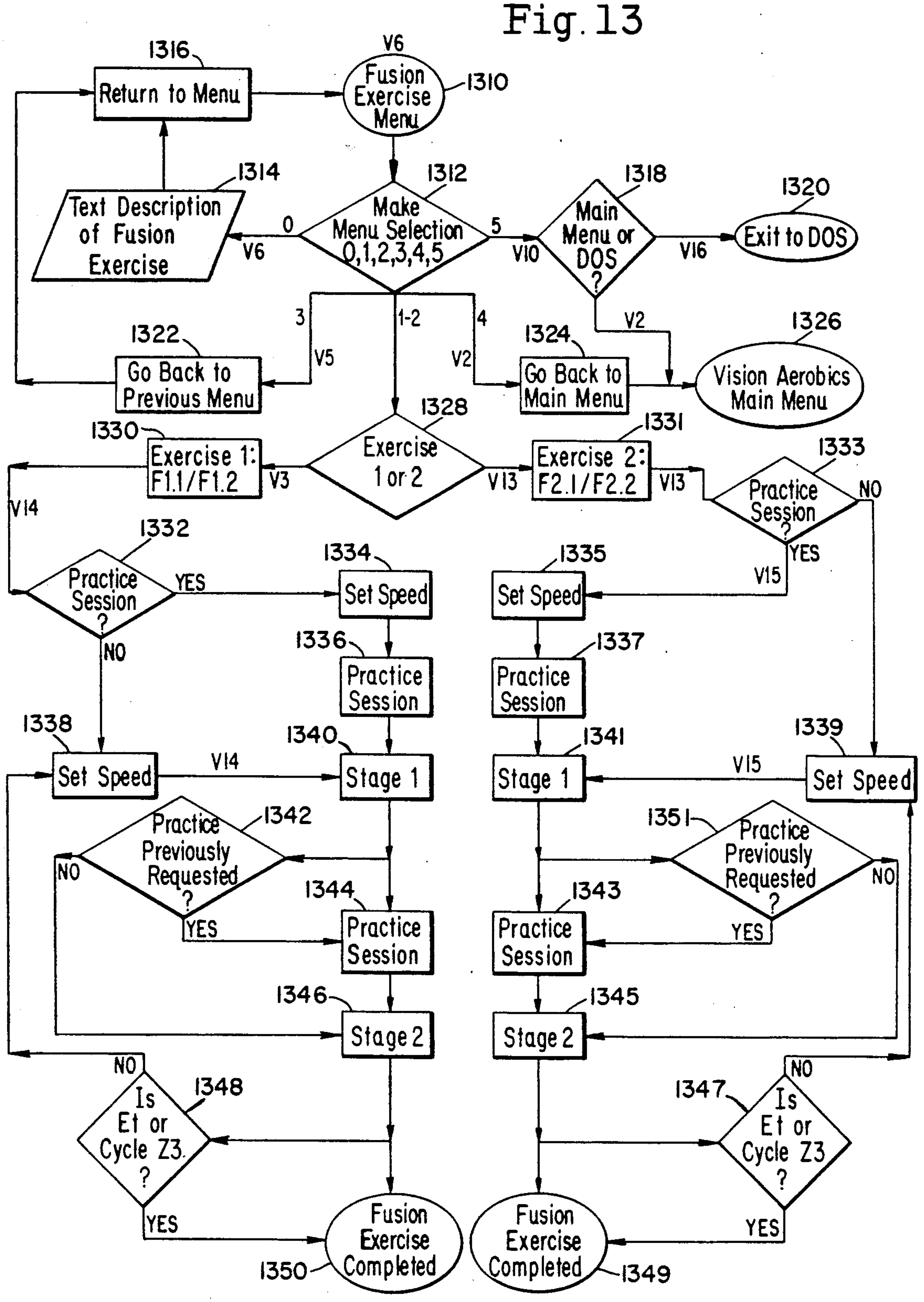
FIG. 13 illustrates the flow diagram of the Fusion Exercise programs.

The object of the Fusion Exercise is to train the eyes to work together more easily. Each eye sees an image. Normally, the visual system joins the two images into a single three-dimensional image. Many people must strain their eyes to join the two images into a single image. The strain on the eyes may show up as a burning or aching sensation, or some other form of discomfort of the eyes. The Fusion Exercises gradually enhance the ability to use both eyes together with less effort and, therefore, less pain and discomfort and greater ability to perform visual tasks. The Fusion Exercises, the flow of which is also illustrated in FIG. 13, are designed to strengthen the eye muscles which are used to produce a single image out of two images.

There are two Fusion Exercises: Exercise F1.1/F1.2 which use block images, and Exercise F2.1/F2.2 in block 1331 which utilizes cone images. As can be appreciated, with reference to FIG. 13, in comparing even-numbered blocks 133214 1350 to the odd-numbered blocks 1333–1349, the flow of the respective programs producing the two Fusion Exercises is identical. The Fusion Exercise could also be done, utilizing differently colored objects moved manually or by power-operated means. However, the preferred mode of accomplishing the exercise is to produce the images on a computer screen, in the form of a progressive interactive quantitative exercise. The Fusion Exercise is done in two stages. The first stage involves convergence or forcing the eyes to cross. The second stage is divergence or forcing the eyes to spread apart. These correspond to the two stages illustrated as blocks 1340 and 1341, respectively, and 1345 and 1346, in FIG. 13.

Figure 14:
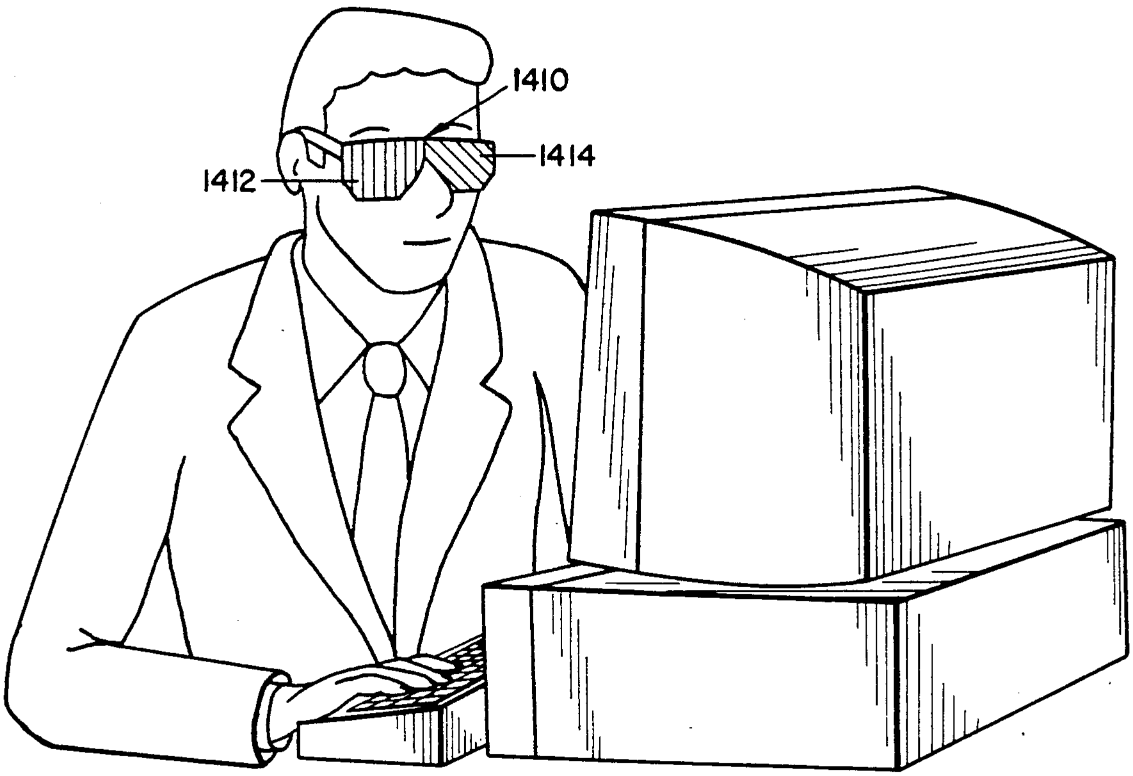
FIG. 14 illustrates the use of red/green glasses in conjunction with the Fusion Exercise programs.

The Fusion Exercises are performed with the user wearing red/green glasses, or similar device, illustrated in FIG. 14 as 1410. The right side of the glasses has a red lens 1412, and the left side of the glasses has a green lens 1414. The Fusion Exercise, using the glasses 1410, is based on the principle that the eyes will track opposite color elements on the screen to that color lens that is before the eye. Glasses 1410 also give a dimensional visual effect to the user viewing the computer screen. The Fusion Exercise, like the Eye Movement Exercise, is a self-contained eye exercise that can be performed independently of any other exercise of the VISION AEROBICS program. However, it is preferred that the user perform the Fusion Exercise along with one of the Eye Movement and Focusing Exercises, at least one time per day for an interval of approximately three minutes. The Fusion Exercise, like the Eye Movement Exercise previously described, is not only an eye exercise, but a progressive and interactive exercise that provides the user with a quantitative measure of progress, both during the exercise and, as it records the exercises over the duration of the period of use of the exercise.

The Fusion Exercise F1.1/F1.2 choice in block 1328 of FIG. 13 will now be described in detail, with reference to FIG. 13 and FIGS. 15–18. As previously discussed, Fusion Exercise F2.1/F2.2, shown in block 1331, is similar to Fusion Exercise 1 in block 1330, both in its flow and its operation, except that cones are used rather than blocks as the projected moving elements on the screen. Fusion Exercise 2 will, therefore, only be discussed briefly after Fusion Exercise 1.

Once the Fusion Exercise 1 is selected in block 1330, the V3 program is run, and data files are opened for the user's scores of each stage of the exercise, to be entered and cross-referenced with corresponding identifiers such as the user's social security number. After displaying a brief explanatory text regarding the Fusion Exercise in block 1330, the V14 program module is run. The V14 program produces a screen similar to that referred to generally as 1510 in FIG. 15. That screen has a green block 1512 and a red block 1514, arranged initially in close parallel relationship, the green block having an X in its center, and a box 1529 above the X. The red block 1514 has an X 1526 at its center, and a circle 1528 below the X. The alignment of three elements can be used to determine the muscular balance between the left and right eyes. In addition, the appearance or nonappearance of all of the elements can be used to determine whether or not the brain is accepting images seen by each of the eyes. Located slightly below the blocks is a measuring grid line 1516, with gradations equally marked on the left and right sides from a center point which is numbered 0. The value of the gradations changes with respect to the speed selected for the Fusion Exercise. Screen 1510 also has a block 1518, indicating which stage of the exercise is being projected. In the upper section of screen 1510, from left to right, are three blocks, the first 1522 being an indicator of the user's score in stage one of the Fusion Exercise. The second 1526 keeps a running total of elapsed time that the user has been performing the Fusion Exercise. The third 1524 is a summary of the score that the user has attained in stage two of the Fusion Exercise.

Figure 15:
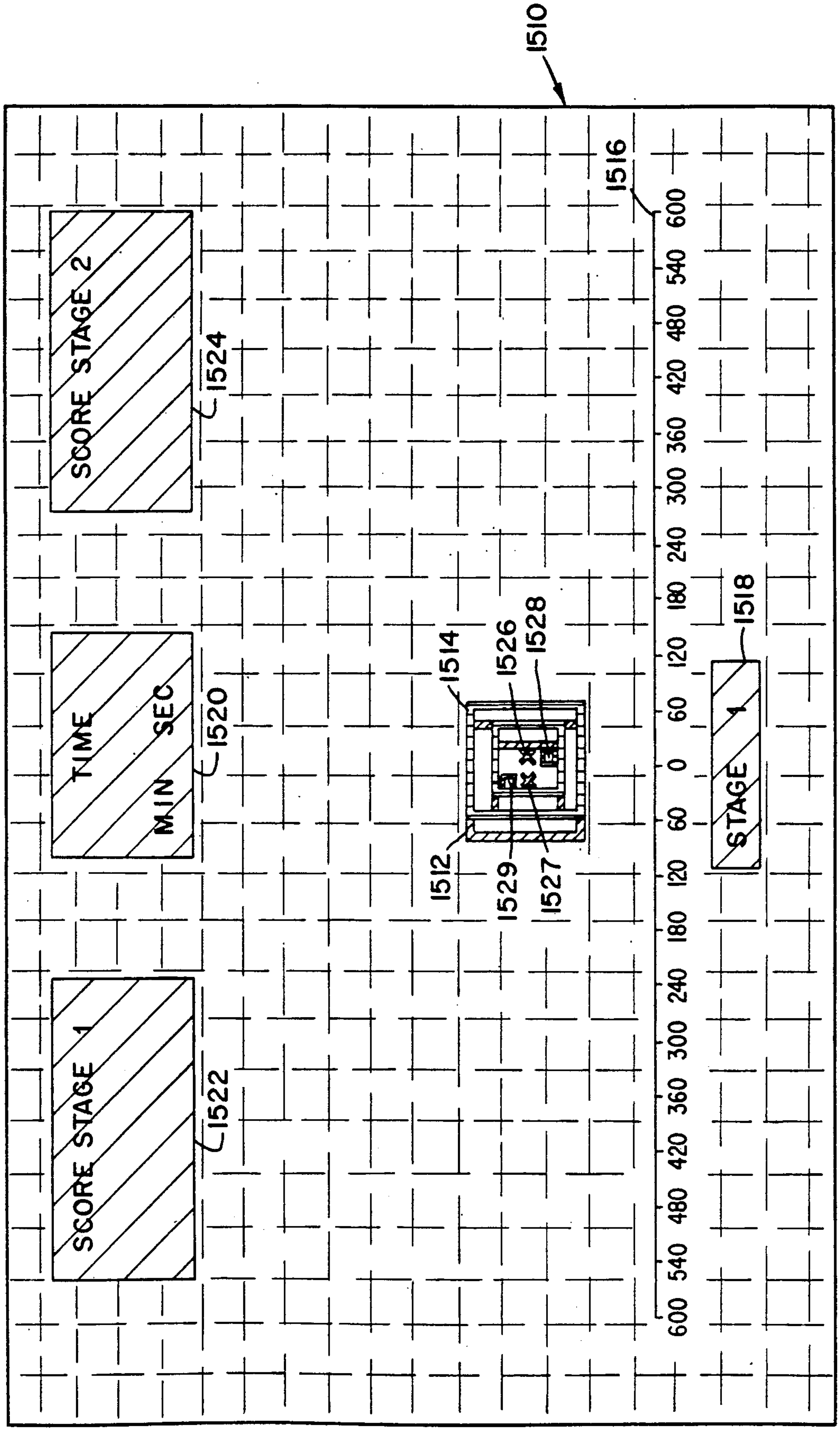
FIGS. 15 and 16 illustrate the screen display generated by Stage 1 of Fusion Exercise F1.1/F1.2.
Figure 16:
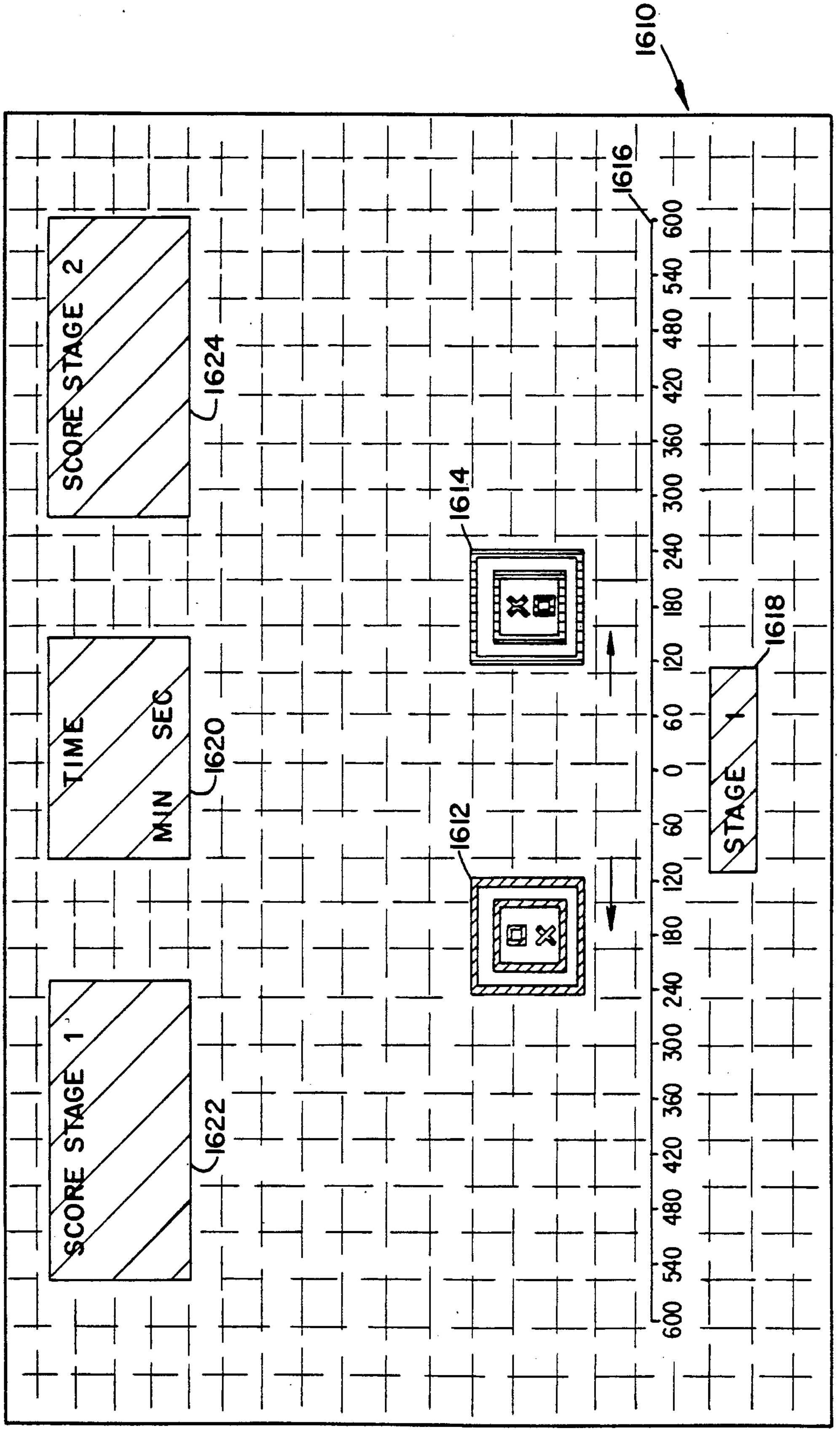
Figure 17:
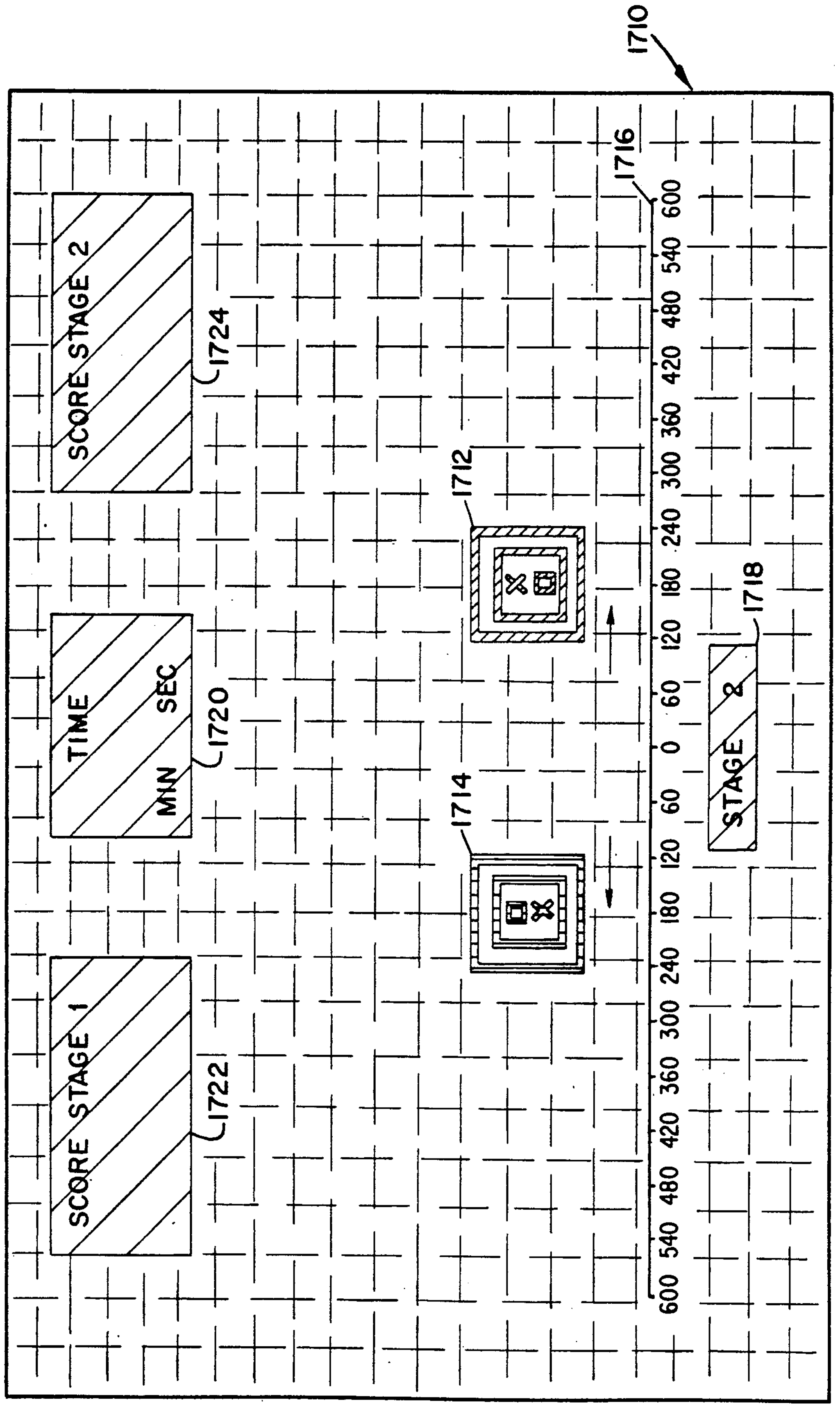
FIG. 17 illustrates the screen display generated by the Stage 2 of Fusion Exercise F1.1/F1.2.

Viewing FIG. 13 in conjunction with FIG. 15, the user is first asked whether he would like to undergo a practice session before beginning the exercise in block 1332. This question is presented to the user on the screen in FIG. 15 in a box positioned just above the two blocks 1512 and 1514. If the user chooses to engage in a practice session first, the V14 program moves to block 1334, in which the V14 program asks the user which of three speeds he would like the blocks to move apart or together. After having set the speed, the V14 program moves to block 1336, and the practice session is begun. The practice session is produced on the screen over a timed interval, such as forty seconds, during which time the blocks are repeatedly moved away from each other and then returned to their original position. Since the user is wearing glasses containing a red lens 1412 in front of the right eye and a green lens 1414 in front of the left eye, as shown in FIG. 14, the eyes will track the opposite color element 1512 or 1514 being projected on the screen. In stage one of the practice session accompanying stage one, this will result in a convergence or a crossing movement of the eyes as the elements 1512 and 1514 are moved away from each other. The practice session offers the added advantage of acclimating the user to the beginning and ending appearance of the exercise.

After the timed practice session, the V14 program sends the user to block 1340. If the user has chosen in block 1332 not to have a practice session, he is asked in block 1338 to set the speed to one of three choices in block 1338, and the user is then also sent to stage one of the exercise in block 1340. Stage one of the exercise, illustrated in block 1340, begins generally as illustrated in FIG. 15, with the green element 1512 and the red element 1514 largely overlying one another, the green element being slightly to the left of center of the screen and the red element 1514 being slightly to the right of the center of the screen. The user is then prompted to hit the spacebar to initiate the exercise.

Once begun, stage one of the Fusion Exercise begins recording the elapsed time of the Fusion Exercise in block 1520. Moving now to FIG. 16, the elements 1612 and 1614 continue to move away from each other at a speed according to that previously chosen by the user. The user is instructed to keep the images the same as when the Fusion Exercise started, that is, the small rectangle in front of the single image. The user is then instructed that when the image breaks into two similar images, he should stop the exercise by pressing the spacebar. Once the image is split and the spacebar is hit, the timer is temporarily halted and the V14 program records a preliminary score for stage one in block 1622, according to the distance along the grid 1616 that the elements 1612 and 1614 have moved, before the user was unable to continue to reconcile the elements into a single image.

The movement of elements 1612 and 1614 in stage one of the Fusion Exercise causes a convergence or crossing of the eyes, since, as stated previously, the user's eyes, using the red/green glasses 1410, track the opposite color element as it moves. The values along the grid vary according to the speed of movement of elements 1612 and 1614 chosen initially by the user. The lower the speed, the higher the value of the increments along grid 1616. This results in a situation where a lower fusion score indicates a more difficult exercise. The user, therefore, obtains a lower score for the same absolute distance of movement, for a higher speed than for a lower speed setting. This is because it is more difficult for the eyes to reconcile two images into one when the two elements are moving away from each other at a higher rate of speed. This also gives the user, and those examining the data, a quantitative measure of one's convergence capabilities and a way to measure quantitative progress in this area.

Once the user has completed stage one (convergence), the Fusion Exercise in block 1340, the V13 program proceeds in block 1342 to examine whether a practice session was requested prior to stage one in block 1332. If a practice session was previously requested, the user is sent by the V13 program to block 1344, to a second practice session prior to engaging stage two of the Fusion Exercise in block 1346. If a practice session was not previously requested, the V13 program sends the user directly to block 1346 and stage two of the Fusion Exercise.

Stage two of the Fusion Exercise involves creating a divergence or a spreading of the eyes in opposite directions. Stage two of the Fusion Exercise, illustrated in FIG. 17, produces a screen 1710, quite similar to the screen produced in stage one. The stage two Fusion Exercise, screen 1710, has a grid with equidistantly spaced gradations 1716 with indicator block 1718, telling which stage of the fusion program is being projected, score blocks for stages one and two 1722 and 1724, respectively, and an elapsed time indicator block 1720. Screen 1710 also has red element 1712 and green element 1714. However, in stage two of the Fusion Exercise, the red and green elements 1712 and 1714, respectively, have their positions reversed to those positions in stage one of the exercise. That is, the green element 1712 is positioned initially slightly to the left of center, and the red element 1714 is positioned slightly to the right of center. The elements then, during the course of exercise, move away from the center of the screen at the same rate, until the user is no longer able to keep them focused as a single image and they split apart. The user is then, again, instructed to hit the spacebar when they split apart, and when this is done, a score is recorded for stage two, according to the distance away from the zero centerline on the grid elements 1712 and 1714 have traveled.

It can be appreciated that since the eyes track opposite color elements, the movement of elements 1712 and 1714 in stage two of the Fusion Exercise causes the opposite eye movement or a divergence of the eyes away from each other rather than the convergent eye movement of stage one of the Fusion Exercise. Once stage two is complete, the V14 program checks the timer and counter in block 1348 to see whether the user has engaged in three minutes of Fusion Exercise, or if three complete cycles (of stage one and two exercise) have been completed. If the user has, the scores from the stage one and stage two of the Fusion Exercise are displayed, and the user is returned to the Main Menu in 1350. If not, the user is then asked to set the speed again in block 1338, and perform a succession of stage one followed by stage two fusion exercises in blocks 1340 and 1346, until he has performed the Fusion Exercise for more than three minutes or three cycles. Then the Fusion Exercise is completed in block 1350, and the scores are displayed.

Figure 18:
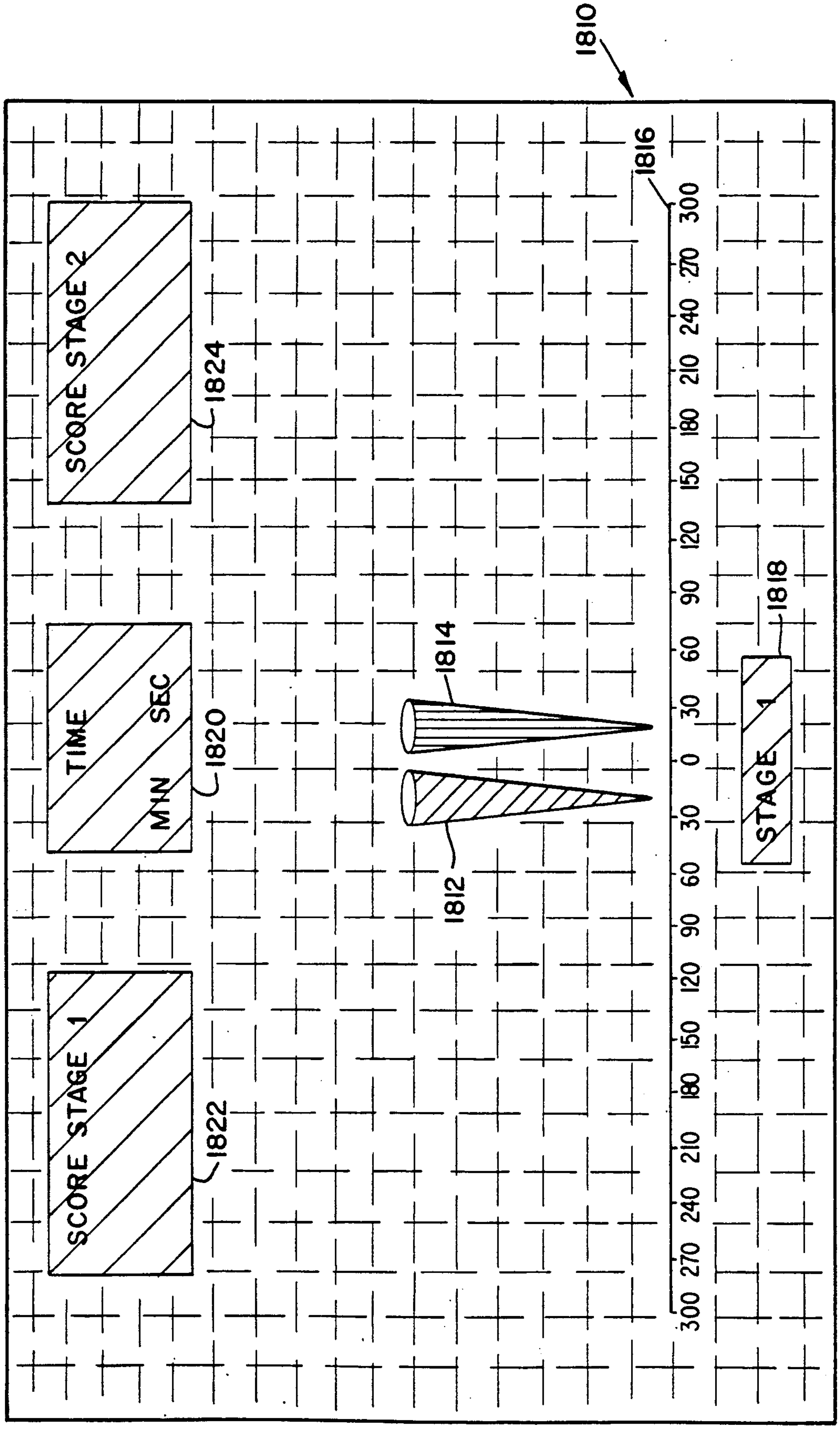
FIGS. 18 and 19 illustrate the screen display generated by Stage 1 of the Fusion Exercise F2.1/F2.2.
Figure 19:
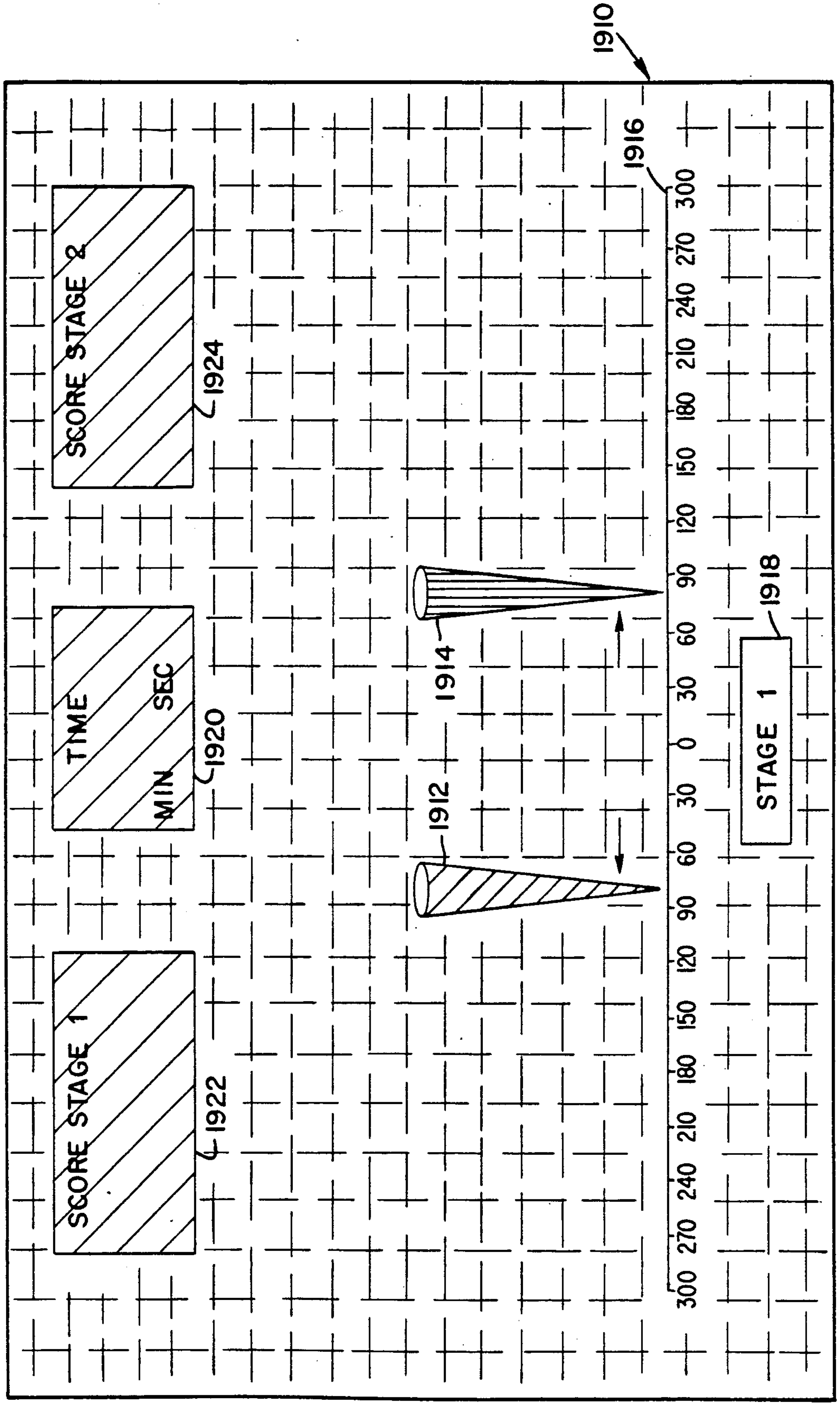
Figure 20:
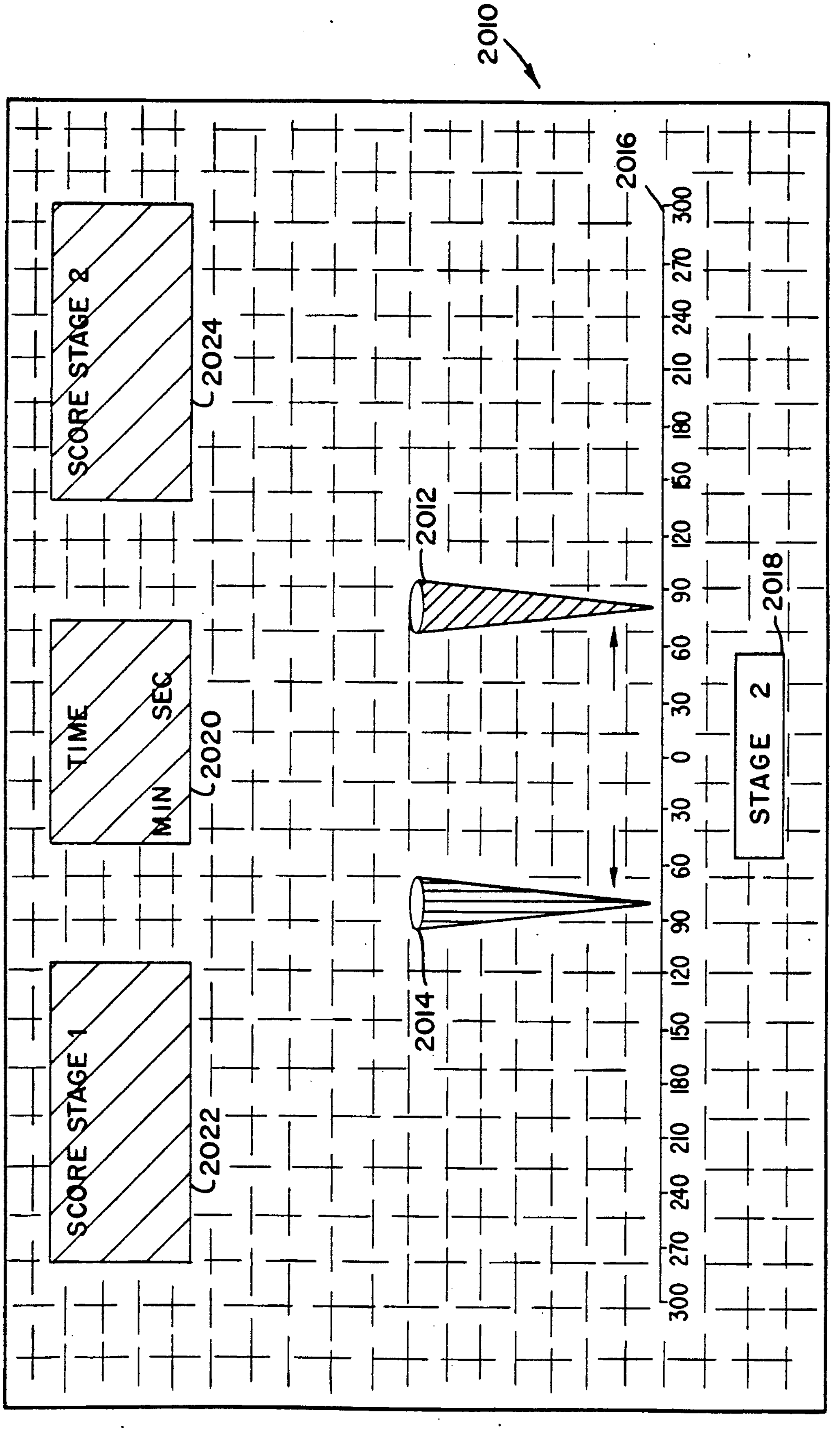
FIG. 20 illustrates the screen display generated by Stage 2 of Fusion Exercise F2.1/F2.2.

Fusion Exercise F2.1/F2.2, illustrated in block 1331 through block 1349, is exactly the same, both in flow and appearance, as Fusion Exercise F1.1/1.2, except that cones are used as elements, rather than the blocks. These colored cones produce the on-screen appearance of the Fusion Exercise illustrated in FIGS. 18–20. It will be noted that the gradations on the grid line 1816, 1916 and 2016 of FIGS. 18–20 are in multiples of ninety. This is because the lowest speed has been chosen for the exercise, and the values of the gradations, therefore, are the greatest possible values.

The Focusing Exercise is the last of the three exercises of the VISION AEROBICS program. As illustrated in FIG. 7, the exercise is accessed by choosing selection three from the Main Menu in block 724. The Focusing Exercise then calls for the V11 program to be run in block 734. The Focusing Exercise, as illustrated both in terms of the flow of the program and the on-screen appearance of the exercise, is, like the two previous exercises, Fusion and Eye Movement, an interactive exercise. The Focusing Exercise, however, is not an exercise that provides the user with a quantitative measure of his initial focusing abilities or his improvement over the duration of use of the exercise. Like the other two exercises, the Focusing Exercise could also be performed manually, using a book or other preprinted form of text. However, the preferred mode is to provide the Focusing Exercise as computer program that generate an interactive screen display that involves approximately three minutes of focusing exercise.

Clear vision depends upon being able to focus your eyes. The closer something is, the more the eye muscles must work in focusing to see it. Reading text or numbers on a video display terminal from twenty inches away requires less focusing and effort that if you are only ten inches from the screen. As individuals get older, the ability of the eye muscles to focus properly becomes more difficult. The Focusing Exercise strengthens the muscles that control focusing skills, and reduces the tendency of the eyes to under or overfocus, which can cause discomfort and blurred vision.

Figure 21:
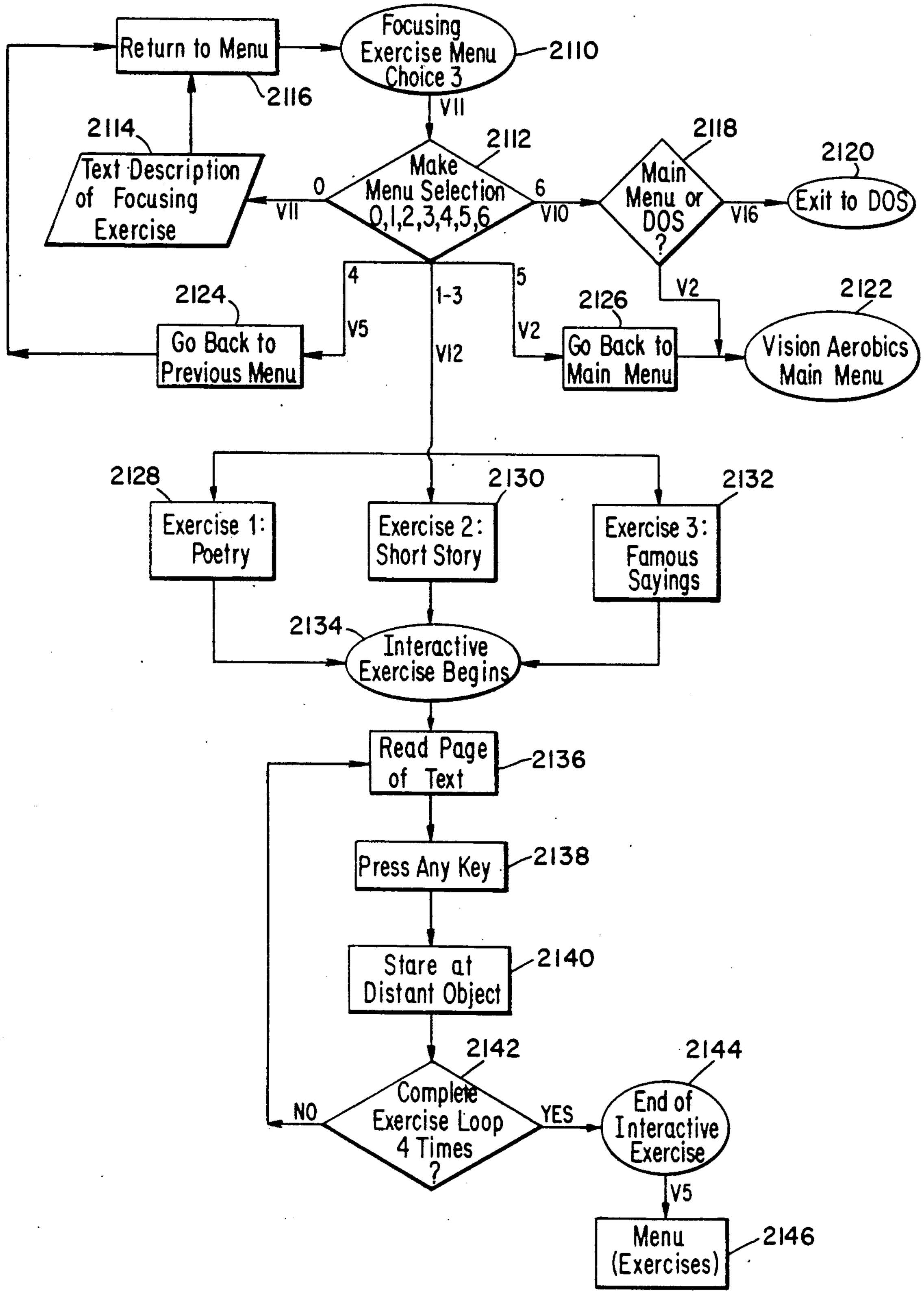
FIG. 21 illustrates the flow diagram for the Focusing Exercise programs.

Turning to FIG. 21, the flow of the Focusing Exercise is illustrated. Once the Focusing Exercise is chosen from the Main Exercise Menu, the Focusing Exercise Menu, which is similar in format to the Main Menu illustrated in FIG. 5, is displayed in block 2110 and 2112. The Focusing Exercise Menu requires the user to make one of seven selections (0–6) in block 2112. If the user makes menu selection 0, the V11 program is accessed, and a text description of the Focusing Exercise is produced in block 2114. After that description is produced, and the user is returned in block 2116 to the Focusing Exercise Menu block 2110. If the user makes menu selection 5, exit, the V10 program is accessed in block 2118, and the user is asked whether he would like to exit to the Main Menu or to the operating system in block 2120, as previously described in blocks 2118 and 2122. Returning to block 2112, if the user makes menu selection 4, go back to previous menu, the V5 program is accessed in block 2124, and the user is returned to the Focusing Exercise Menu of block 2110 by block 2116. If the user makes Main Menu selection 5 in block 2112, the V2 program is run, and the user is returned by block 2126 to the VISION AEROBICS Main Menu in block 2122. If the user in block 2112 selects option 1, 2 or 3, the three Focusing Exercises, poetry, short story, or famous sayings in blocks 2128, 2130 and 2132, respectively, the interactive Focusing Exercise is begun in block 2134.

Figure 22:
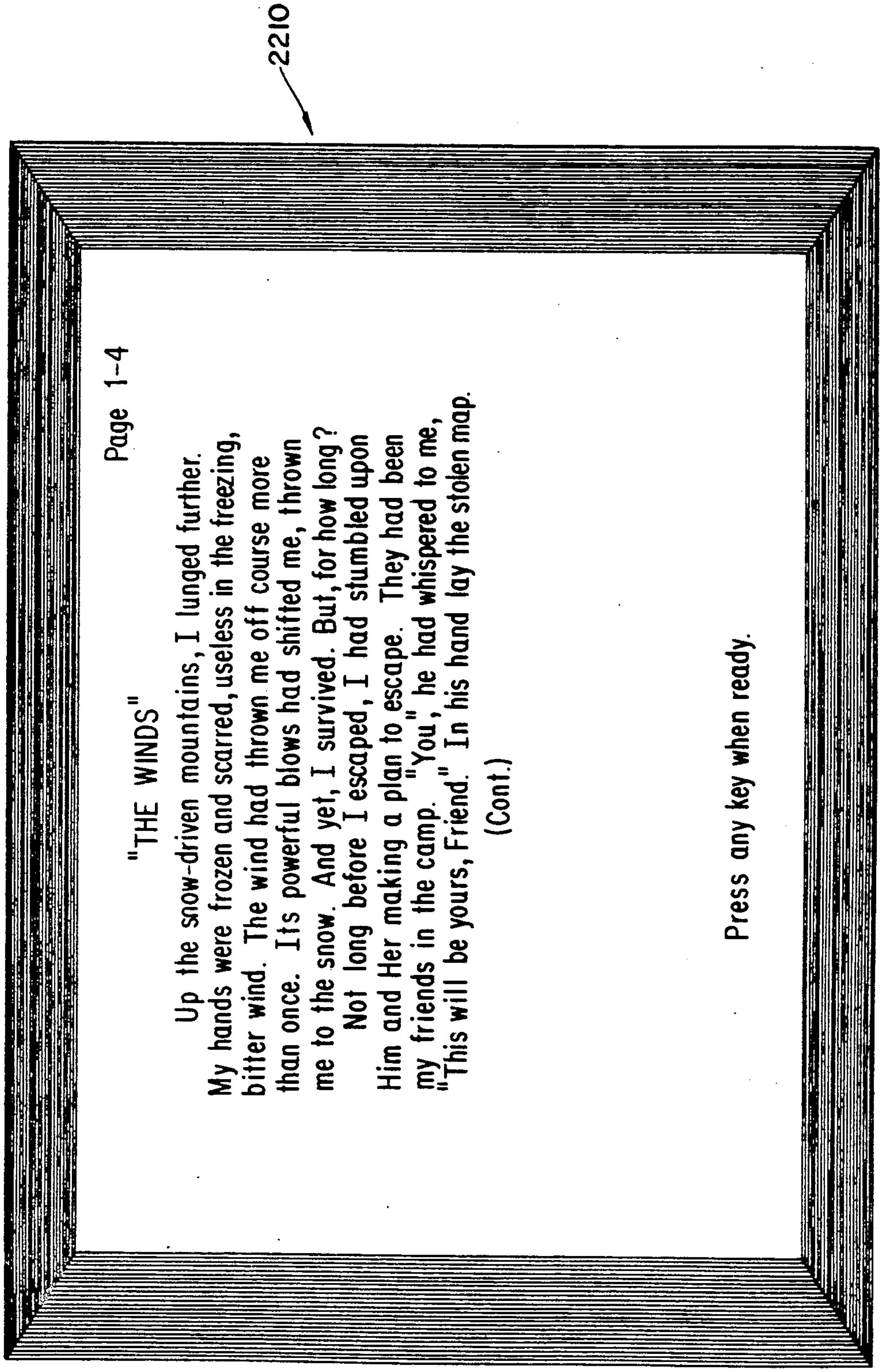
FIGS. 22 and 23 illustrate exemplary screen displays generated by the programs of the Focusing Exercise.
Figure 23:
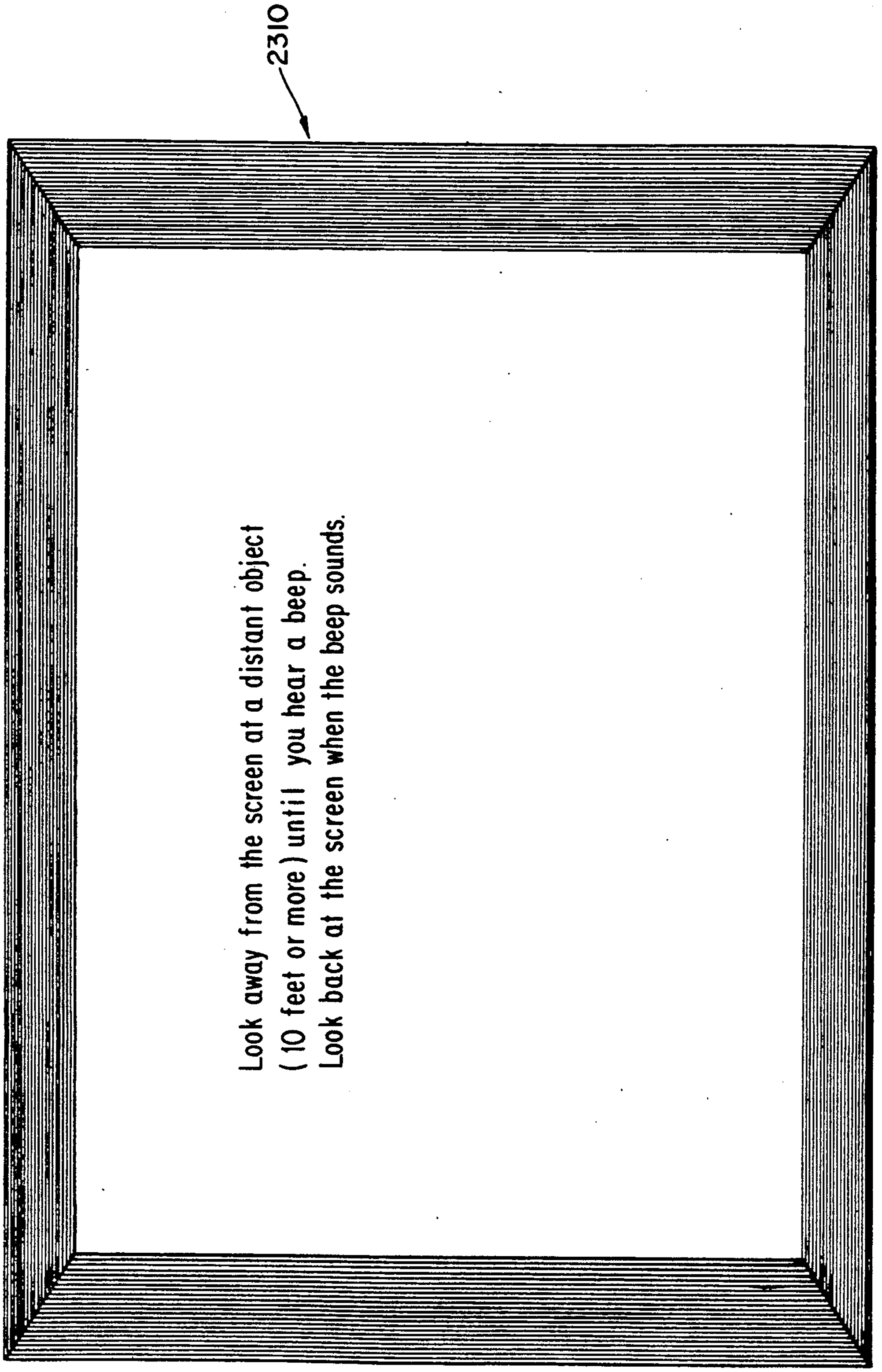
Figure 24:
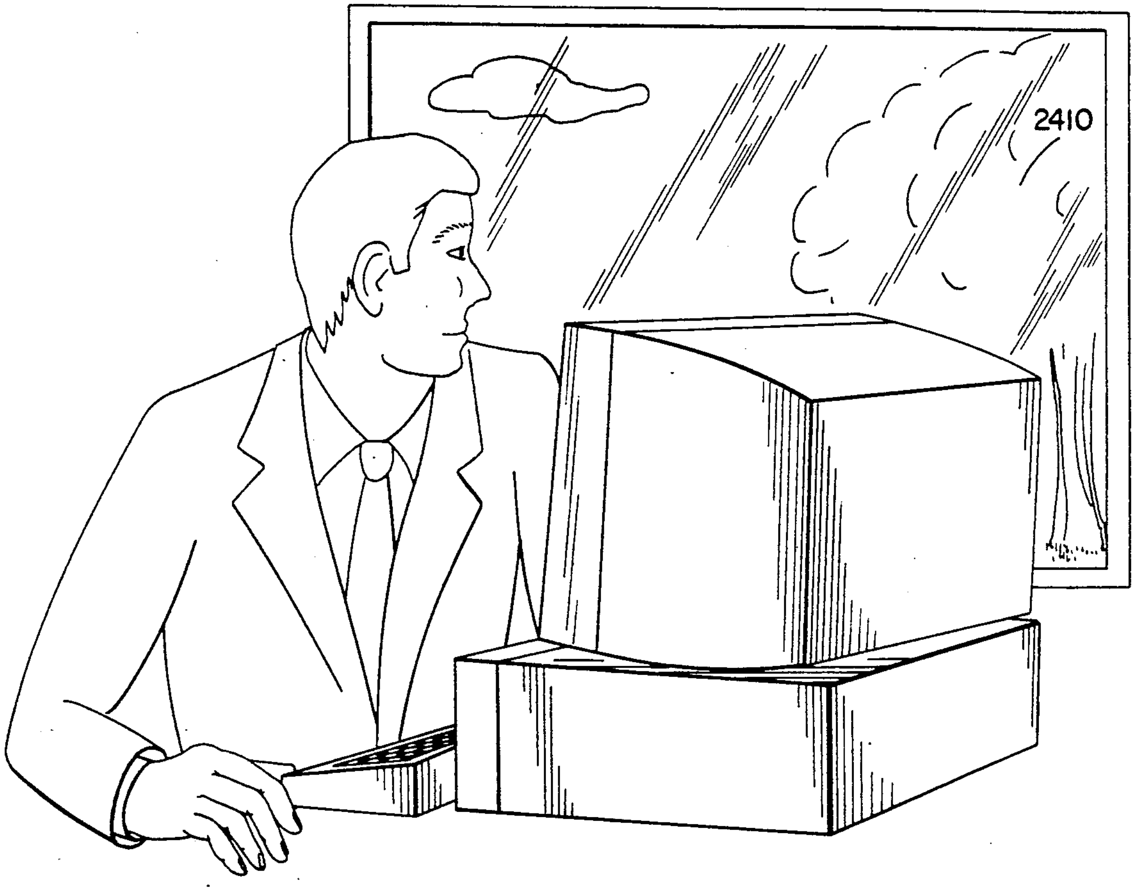
FIG. 24 illustrates an individual using the Focusing Exercise of the present invention.

The exercise begins by displaying the first of four pages of text in block 2136, the subject matter of which is determined by the menu selection made in block 2112. An exemplary screen display is illustrated in FIG. 22 as 2210. The user is given up to one minute to read the page of text. If the user is finished reading the page of text prior to the one-minute time limit, he is instructed on the screen to press any key when ready. This is also illustrated in block 2138 of the Focusing Exercise flow diagram in FIG. 21. Once the user has either pressed a key, signifying he is done reading the text, or one minute has expired, the V12 program displays a second screen which instructs the user in block 2140 to stare at a distant object. That second screen is illustrated in FIG. 23 as 2310. FIG. 24 illustrates a user engaging in the second phase of the Focusing Exercise, staring at a distant object 2410. It should be noted that the user must look at an object at least ten feet away during the second phase of the Focusing Exercise. The V12 program activates a timer that runs ten seconds and sounds a beep at the end of the tensecond duration. The user is instructed to look back at the screen when the beep sounds.

Returning to FIG. 21, the V12 program in block 2142 establishes a counter that increases by one each time the user has completed the two phases of the Focusing Exercises in blocks 2136–2140. The V12 program in block 2142 checks that counter to see if the exercise loop has been completed four times. If it has not, the program returns the user to block 2136, to engage in another two-phase loop of Focusing Exercise. If the user has already completed four loops of exercise, the V12 program ends the Focusing Exercise in block 2144, and accesses the V5 program to display the exercise menu in block 2146.

As can readily be appreciated, the subject matter of the text presented in the Focusing Exercise can readily be changed or customized. This is done by going back into the program, removing the existing text and replacing it with another selected reading.

MAIN MENU CHOICE 3—SCORING REVIEW

Figure 25:
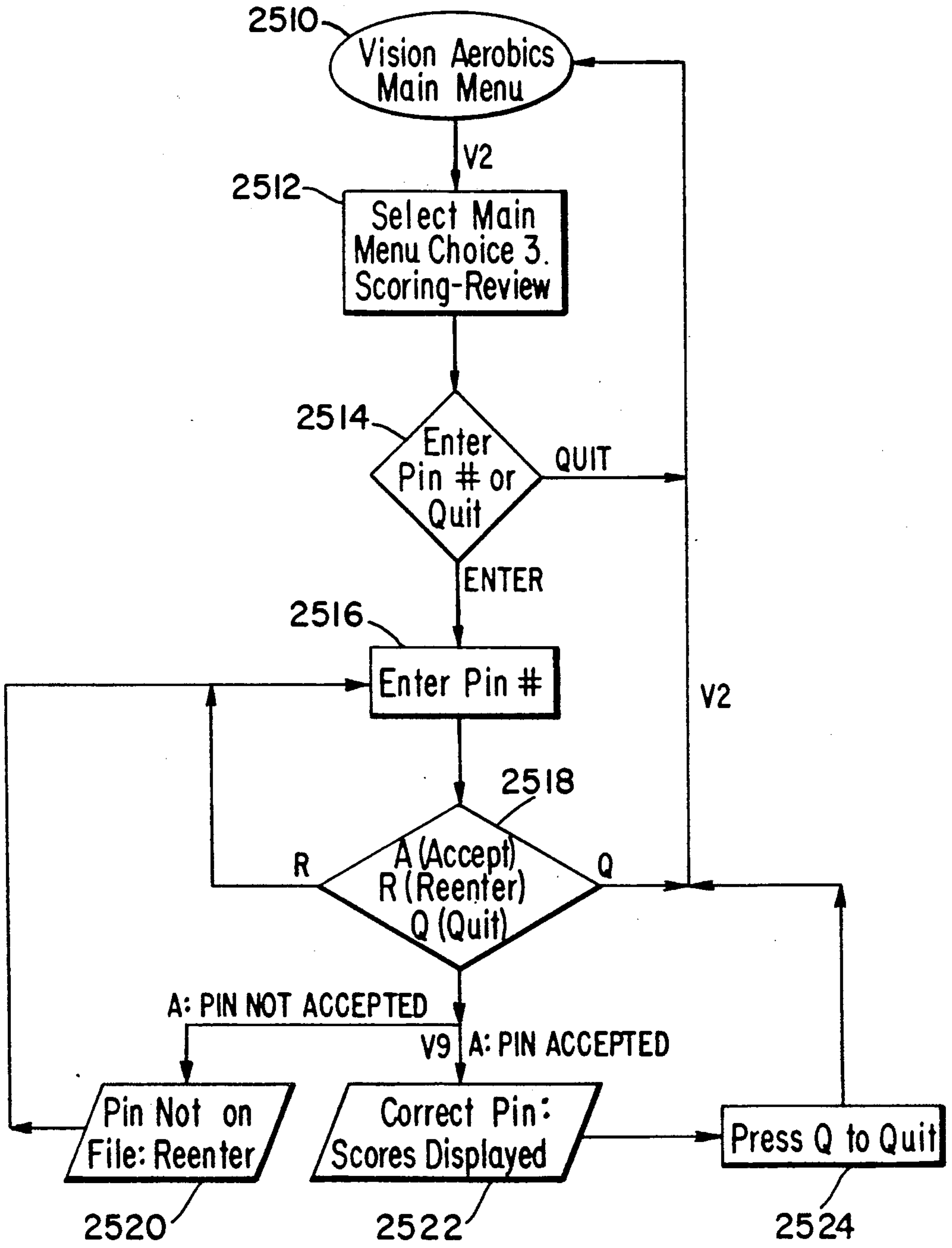
FIG. 25 illustrates the flow diagrams for the Main Menu Choice 3 Scoring—Review.

Returning to the VISION AEROBICS Main Menu, as illustrated in block 2510 of FIG. 25, the third choice, scoring review, will now be discussed. If the user makes the third choice from the Main Menu in block 2512, the V2 program progresses identically to the way that it did when Choice 2, the exercise (scored), was selected. That is, on making Choice 3, the user is requested to enter his personal ID number or press Q for quit in block 2514. If the user chooses to quit, he is returned to the VISION AEROBICS Main Menu in block 2510. If the user enters a PIN number in block 2516, the V2 program then requests the user in block 2518 to enter A to accept the PIN number, or to re-enter the PIN number, or Q to quit the V2 program. If the user in block 2518 enters Q to quit, the user is returned to the VISION AEROBICS Main Menu in block 2110. If the user has noticed that he has entered the PIN number incorrectly, he may press re-enter in block 2518, and the V2 program returns him to block 2516, where he must enter the correct pin number. If the user in block 2518 presses the Choice A, to accept the PIN number, the V2 program will then compare the PIN number entered to that which was originally put on file when the user first accessed the system. If the PIN number does not correspond to that which was originally entered, the V2 program in block 2520 displays the message that that PIN number is not on file, and returns the user to block 2516 to re-enter the PIN number. As a security device, the number of times that an incorrect PIN number is allowed can be set between one and infinity in the V2 program. If the PIN number entered in block 2516 is found by the V2 program to be the same as that entered initially, the PIN number is accepted, and the V9 program is accessed.

Figure 26:
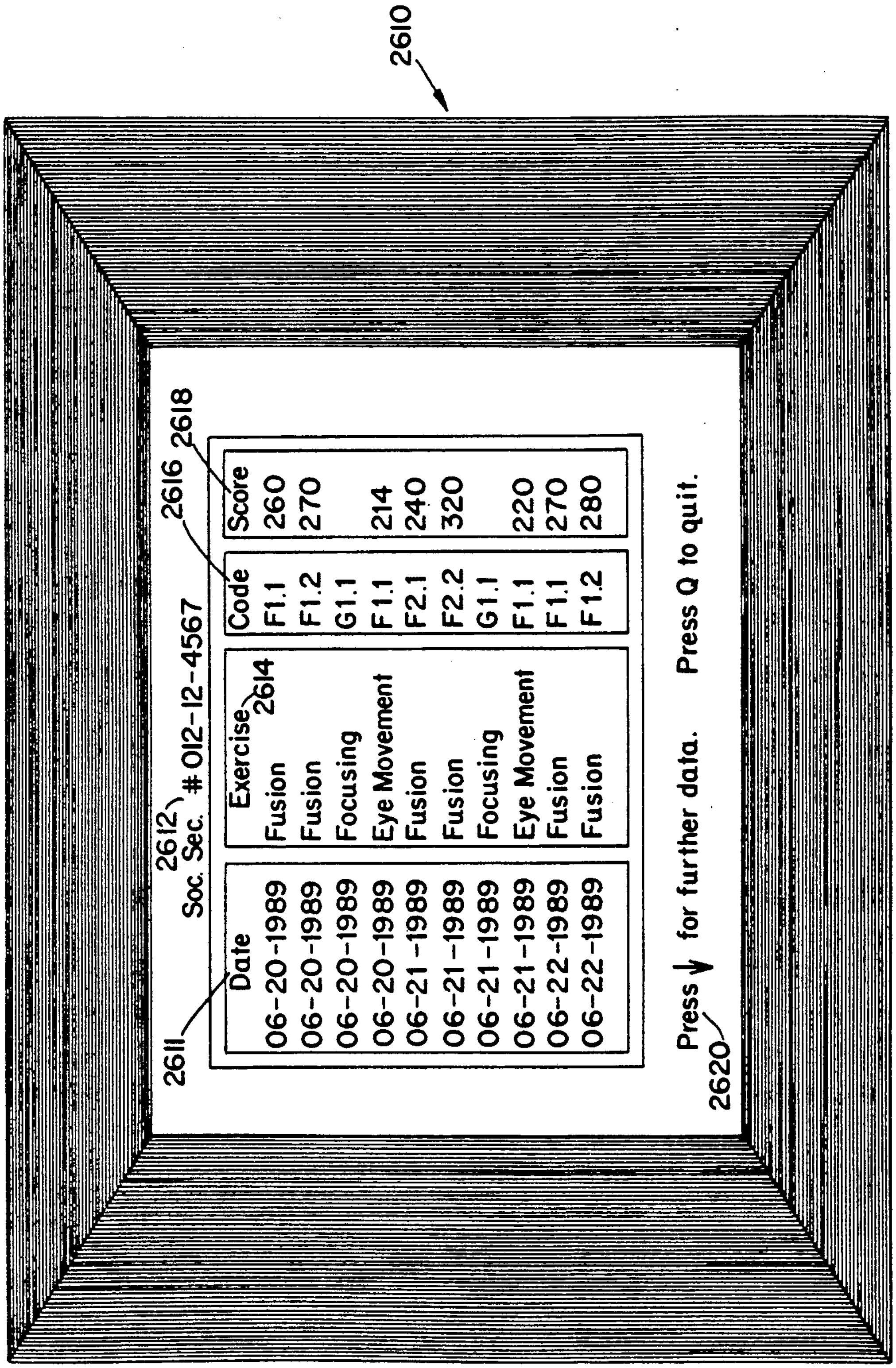
FIG. 26 illustrates the screen display generated by the Main Menu Choice 3 Scoring—Review.

The V9 program module accesses and displays the data in the form of scores recorded from previous exercises engaged in by the user. The format of the V9 screen display is illustrated in FIG. 26, generally as 2610. The data is categorized under the user's social security number 2612, and displays the dat 2611, exercise 2614, code of the exercise 2616, and the score 2618 obtained in chronological order from top to bottom. If there is more than one full screen of data or scores from exercises previously done by the user, a message 2620 instructs the user to press an upward or downward arrow on the keyboard to show a previous or next page of data. The data will be displayed for thirty seconds, or until the user presses Q to quit the data. If the user presses Q to quit the data in block 2524 of FIG. 25, the user is then returned to the VISION AEROBICS Main Menu in block 2510. Main Menu Choice 3, which accesses the program V9, gives the user a review of his scores and progress, over time, in completing the three exercises of the VISION AEROBICS program, in a legible and easy to understand format.

Main Menu Choice 3 allows the user, upon proper entry of a PIN number, to access his own scores. He cannot access the scores of any other user without knowing their PIN numbers. System-wide data on all users of the VISION AEROBICS program is dumped into a secure "black box". That black box can only be accessed by a system controller using the Report.1, Report.2 and Report.3 programs discussed later in detail.

MAIN MENU CHOICE 4—MASTER PASSWORD CHANGE

If the user in block 24 of FIG. 1 chooses Main Menu Choice 4—Master Password Change, the Vision. Rep. program (not illustrated) is accessed in block 36. That program simply calls for a new password to be entered, and creates a data file to hold that password and cross-references it with the user's social security, personal and scoring data. It then takes the old password and erases it, replacing it with the new password, so that the data will require the new password to be entered to access for any future data access.

MAIN MENU CHOICE 5—PERSONAL PROFILE

Figure 27A:
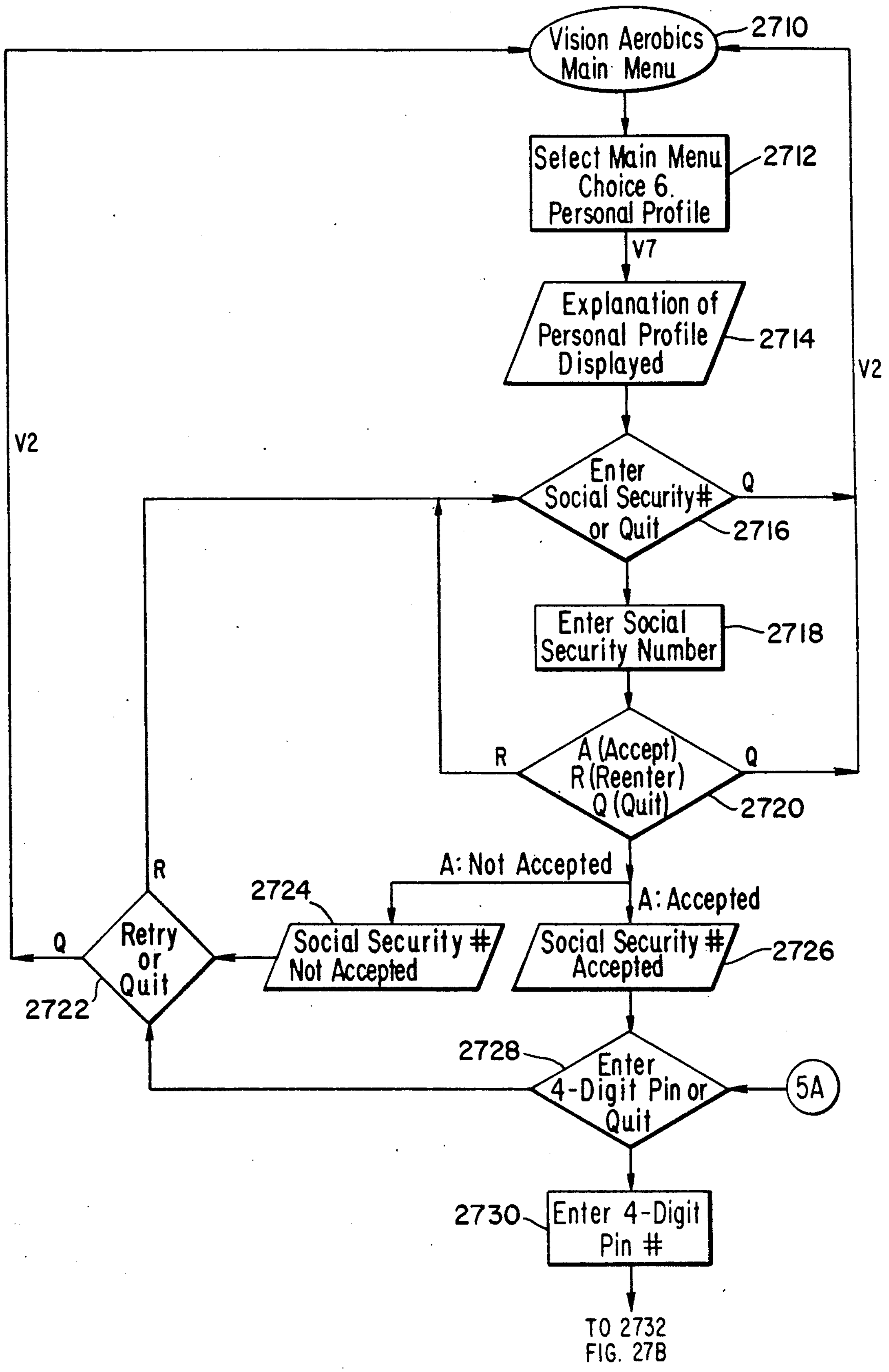
FIG. 27 A–C illustrate the flow diagram for the Main Menu Choice 5 Personal Profile.
Figure 27B:
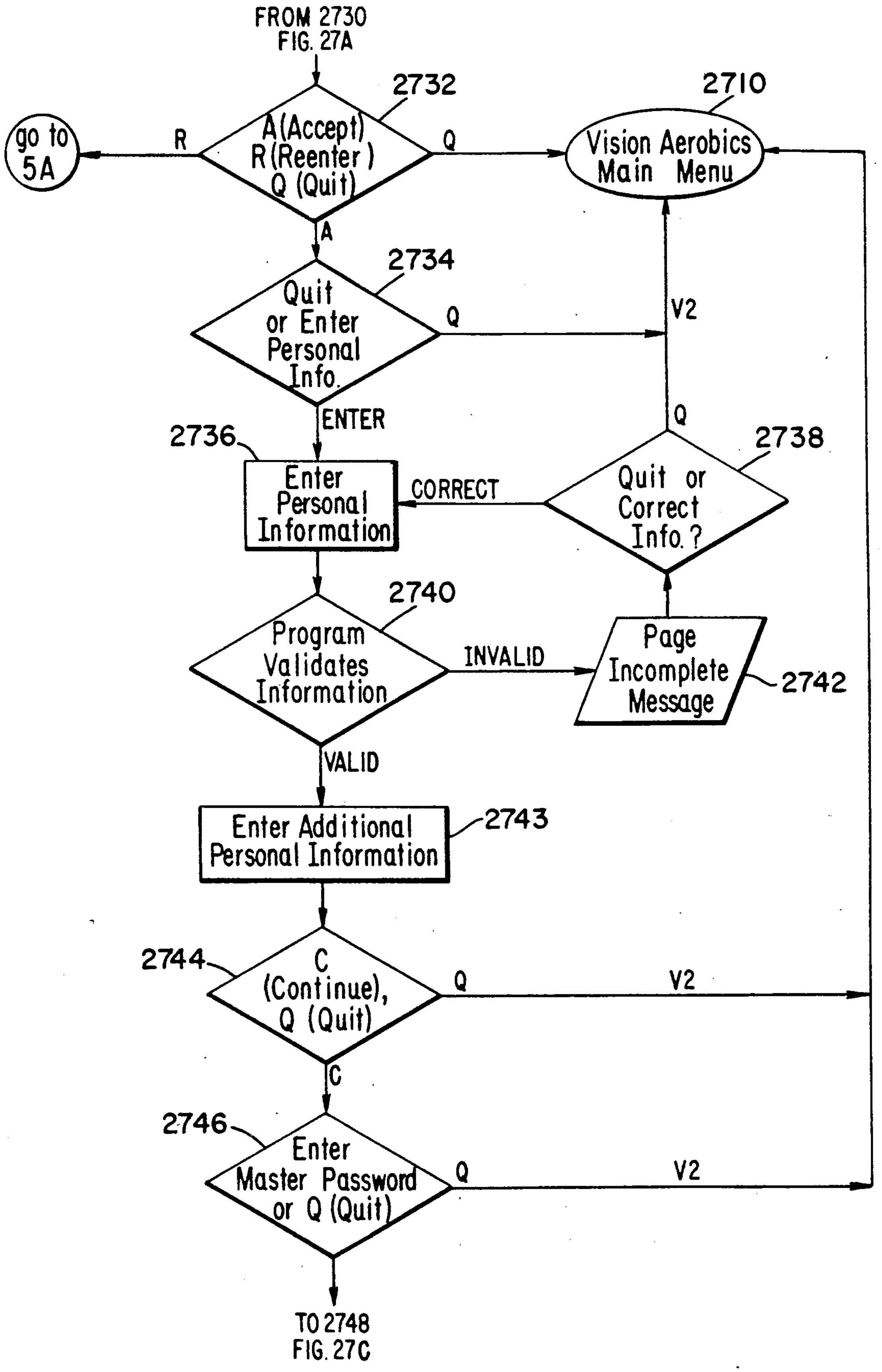
Figure 27C:
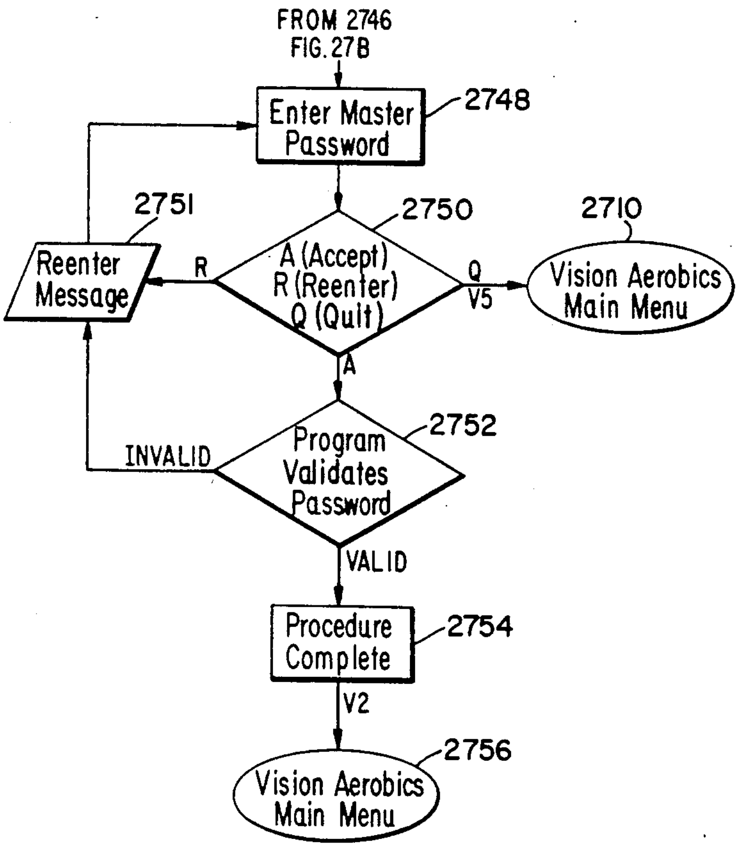

Main Menu Choice 5, the flow of which is illustrated in FIGS. 27A, 27B and 27C, is a procedure for the introduction of an additional user to the VISION AEROBICS system after the program has been accessed by an initial user. It consists of entries of the user's social security number, personal ID number, miscellaneous personal information, and the master password, initially inputted by the first user. When all of the entries are complete, the additional user is able to access the VISION AEROBICS program by typing in just his PIN number. The entries of the social security number and master password allow the user to have a level of security, since the exercise and scoring programs are not able to be accessed without their entry. The personal information allows data collection and analysis of the scores of the user, in conjunction with the answers given to various personal questions, such as use of eyeglasses or amount of time working on a video display terminal, for possible relationships. The social security number allows the data files to be set up and referenced for future data access under the user's social security number.

Main Menu Choice 5, the personal profile, is contained in the V7 program, which is accessed by making Choice 5 on the VISION AEROBICS Main Menu. The V7 program is similar in almost all respects to the V1 program, except that it allows a second user to access the program, other than the initial user who has completed similar data entry procedures in the V1 program. This is illustrated in FIG. 27 A by blocks 2710 and 2712.

Once the user has selected the personal profile, the V7 program is accessed, and it first displays an explanation of the data which will be required to be entered in the course of the personal profile. The user is then asked to make a series of entries of data, beginning with his social security number in block 2716. If the user desires to terminate entry of personal profile data at that time, he may press Q and will be returned to the VISION AEROBICS Main Menu by the V2 program. If the user enters his social security number in block 2718, he is then asked to press A to accept, R to re-enter, or Q to quit in block 2720. If the user chooses to quit in block 2720, the V2 program is also accessed, and the VISION AEROBICS Main Menu is displayed. If the user chooses R to re-enter in block 2720, he is returned to block 2716 to re-enter his social security number. If the user presses A to accept in block 2720, the social security number is accepted and a data file is created to hold the social security number in block 2726. The social security number will then be cross-referenced with future scores from the exercises from that user.

The user is then prompted in block 2728 to enter a four-digit personal ID number or quit the program. If he quits the program, he is returned by the V2 program to the VISION AEROBICS Main Menu in block 2710. If the four-digit PIN number is entered in block 2730, the user in block 2732 is requested to accept or to re-enter Q to quit. If the user in block 2732 presses Q to quit, the V2 program is accessed and the VISION AEROBICS Main Menu is produced. If the user chooses R or re-enter in block 2732, the user is returned to block 2728 to re-enter the four-digit PIN number. If the user presses A to accept, the PIN number is written into a data file for future comparison with the data number entered when the user tries to access the VISION AEROBICS program.

After the user's entry of the personal ID number and its acceptance, the user is requested in block 2734 to either enter other personal information or enter Q to quit. If the user enters Q in block 2734 to quit, the V2 program is run, and the VISION AEROBICS Main Menu is produced. If the user continues in block 2736, he is requested to enter the personal information called for. This includes the year of birth, sex, year started working at the company and department, years he has worn eyeglasses and worked with a computer, and how many hours per day he works with a computer. When this personal information is entered, the V7 program in block 2740 checks to see that information has been entered to each of the personal data inquiries. If all of the inquiries have hot been answered, the V7 program displays a pageincomplete message in block 2742, and sends the user to block 2738 where the user is given the option of quitting and returning to the VISION AEROBICS Main Menu, or correcting or entering additional information. Once the inquiries in block 2736 and 2740 are completely answered, the V7 program moves to block 2742 and requests the user to select from two groups of adjectives which describe the user's feelings about working with a computer. Group One contains the words: challenging, exciting and pleasant. Group Two contains the words: stressful, fatiguing and boring. The user is requested to enter in block 2742 the group number corresponding to the group which best describes his feelings. Once the group number is entered, the user is prompted in block 2744 to press C to continue or Q to quit. If the user presses Q to quit, the V5 program is accessed, and the VISION AEROBICS Main Menu is produced. If the user presses C to continue, the V7 program requests the user to enter his master password in block 2746, or press Q to quit and return to the VISION AEROBICS Main Menu by the V2 program.

Moving now to FIG. 27C, once the user enters the master password in block 2748, he is requested in block 2750 to enter A to accept the password, R to re-enter, or Q to quit the V7 program. If the user enters Q to quit, the V5 program is accessed and the user is returned to the VISION AEROBICS Main Menu in block 2710. If the user enters R for re-enter, he is returned via block 2752 to the master password screen in block 2748, to re-enter the password. If the user chooses to enter the password, he enters A to accept in block 2750, and the V7 program moves to block 2752 and checks the password against the password on file. If the password is not the same as the one on file, it sends the user back to the re-enter message in block 2750, and requests the user to enter the password again in block 2748. If the password is the same as the one previously entered by the user, the program validates the password and moves to block 2754, where the user is instructed that the personal profile procedure has been completed, and instructs the user to hit any key to continue. The V5 program is accessed and the VISION AEROBICS Main Menu is produced in block 2756.

As can readily be appreciated, the data or inquiries requested in the personal profile, can be modified, depending upon the type of information or cataloging or cross-referencing desired by a given user of the VISION AEROBICS system. The personal profile information can be cross-referenced and correlated with the scores attained by the user, to attempt to show correlations between results of the progressive exercises and the responses to the personal profile inquiries.

MAIN MENU CHOICE 6—EXIT

Figure 28:
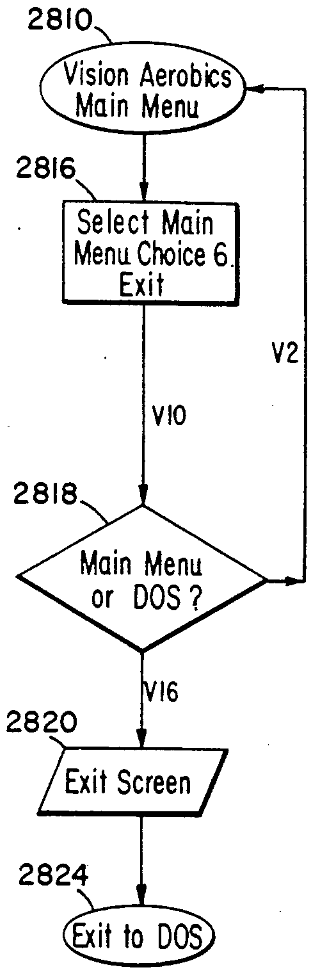
FIG. 28 illustrates the flow diagram of the Main Menu Choice 6 Exit.

Moving now to FIG. 28, the Flow Diagram for the VISION AEROBICS Main Menu Choice 6—Exit, is illustrated. The exit program has been referenced and described many times throughout the detailed description, and is used in many different parts of the VISION AEROBICS program. The exit program is specifically used in conjunction with the V4 program, if no user response is entered within thirty seconds, and also in response to a quit instruction. Once the menu Choice 6 exit is selected from the VISION AEROBICS Main Menu in block 2816, the V10 program is run, and the user is presented with the decision screen, illustrated in block 281 that requests the user to select exiting to the Main Menu or to the operating system of the computer. If the user chooses to exit to the Main Menu, the V2 program is accessed, and the user is returned to the VISION AEROBICS Main Menu in block 2810. If the user chooses to exit to the computer operating system, the V16 program is accessed, the VISION AEROBICS title screen is produced in block 2820, and the user is exited to the computer operating system in block 2824.

THE REPORT PROGRAMS

The Report Programs, previously referred to in conjunction with the scoring review, consist of three separate modules: Report.1, Report.2, and Report.3. The Report.1 program enables a transfer of data from the score or data files which have been created every time the user has engaged in one of the VISION AEROBICS exercises. These programs allow a secure "black box" type storing of data on all users of the VISION AEROBICS exercises and analysis of that data. The Report.1 program opens the score and biographical data files, and allows the data in those files with the identifying social security or biographical information to be transferred to an external memory, such as a floppy disk.

The program Report.2 produces a summary of all activity regarding the use of exercises in the VISION AEROBICS program. The Report.2 program first opens the biographical and score data files and then determines the number of times the exercises have been used. The Report.2 program then goes on to search all scores and produce the lowest score, the highest score, and the average score for each exercise. The Report.2 program also computes the first and last scores for the users of the system. Like the Report.1 program, this data can be read to an external memory device, such as a floppy disk.

The Report.3 program again opens the scoring and biographical files and produces a report on the data. The first segment of the report has to do with the frequency of use of the exercises, including the number of employees and number of times each exercise has been used over a past period of time. It then computes the average number of times each exercise has been used by an employee over that period of time. The program then goes on to show the range of scores and average scores for the past period. The Report.3 program then analyzes the percent change in the scores for all users, and then breaks that down according to the biographical information that was entered in the personal profile, such as the user's sex, age, use or non-use of eyeglasses, or continued use of VDT terminals, and correlates that against the scores obtained. The programs Report.1, Report.2 and Report.3 strictly involve the analysis of data obtained as a result of completing the three exercises.

Other aspects, objects and advantages of this invention can be attained through a study of the drawings, the description, and the appended claims, by one of ordinary skill in the art, without departing from the spirit and scope of the invention as described.

We claim:

1. A method of exercising the eye muscles of a user of a computer connected to a computer display terminal having a screen, comprising the steps of:
- displaying a background on the screen;
- displaying an object at a first random location on the background to stimulate the eye muscles of the user to move the eyes to the first random location;
- removing the displayed object from the screen;
- requesting a response corresponding to the object displayed on the screen within a first time period;
- sensing any user response made within said first time period identifying the object on the screen; and
- recording any response identifying the object entered within the first time period and comparing the object identified by the response entered to the object displayed.

2. The method of claim 1, further comprising the steps of:
- determining and recording the elapsed time of the exercise;
- repeating said steps of displaying a background, displaying an object but at a second random location, to stimulate the eye muscles to move the eyes to a second random location,
- removing the second displayed object, requesting a response to the second displayed object, sensing a user response to the second displayed object, recording the user response and comparing the object identified at the second random location to the object displayed at the second random location and repeating the steps at additional random locations such that the eye muscles will be stimulated to move the eyes around the screen until the elapsed time has reached a pre-determined interval.

3. The method of claim 2 wherein the elapsed time pre-determined interval is about three minutes.

4. The method of claim 1 or 2, further comprising the steps of:

assigning a quantitative value to each response identifying an object on the screen that corresponds to an object displayed on the screen in said comparing step and a code identifying the user to the quantitative value; and storing the quantitative value with the code in a memory.

5. The method of claim 4, further comprising the step of:

displaying a plurality of personal data questions;

recording and storing responses to personal data questions in a memory by the user; and cross-referencing said responses to personal data questions by the user with said quantitative values and said codes in said memory.

6. The method of claim 2, wherein:

said first time period of said step of requesting a response is about two seconds.

7. An interactive progressive method of exercising the eye muscles of a user of a computer connected to a computer display terminal having a screen, comprising the steps of:

providing a plurality of choices of background to be projected on the screen of progressive difficulty that require varying levels of eye concentration for the eyes to perceive an object displayed against the background;

providing a plurality of choices of a given number of different objects to be projected against the background on the screen in the exercise;

providing a plurality of choices of the length of time the given objects will be displayed;

selecting a background, a given number of different objects and a length of time the objects are to be displayed from the plurality of choices;

displaying a background on the screen corresponding to that selected from said plurality of choices of background;

displaying one object on the screen from said given number of different objects selected from said plurality of choices of a given number of different objects to be projected and for a length of time corresponding to that selected from said plurality of choices of the length of time the object will be displayed to require the eyes to concentrate to find the object against the background and stimulate the eye muscles of the user to move the eyes to the location of the object on the screen;

removing the displayed object from the screen;

requesting a response corresponding to the object displayed on the screen within a first time period;

sensing the user response identifying the object on the screen;

recording any identifying response of the user entered within the first time period; and comparing the identified object sensed in the user response to the object displayed.

8. The method of claim 7, further comprising the steps of:

determining and recording the elapsed time of the exercises; and repeating said steps of displaying a background, displaying an object, at additional random locations to stimulate the eye muscles of the user to move the eyes to additional random locations, removing the displayed object, requesting a response of the user to the object displayed until the elapsed time reaches a predetermined interval.

9. The method of claim 8, wherein:

said pre-determined elapsed time interval is about three minutes.

10. The method of claim 7 or claim 8, further comprising the steps of:

assigning a quantitative value to each response correctly identifying an object on the screen in said comparing step depending upon the background, given number of different objects to be projected on the screen, and the length of time the objects will be displayed, that have been selected assigning a code identifying the user to the quantitative value; and storing the quantitative value with the code in a memory.

11. The method of claim 10, further comprising the step of:

displaying a number of personal data questions;

recording and storing any responses by the user to personal data questions in a memory; and cross-referencing said responses to personal data questions by the user with said quantitative value and said code in said memory.

12. The method of claim 8, wherein said first time period in said step of requesting a response is about two seconds.

13. An apparatus for exercising the eye muscles of a user of a computer screen, comprising:

means for displaying a background on the computer screen;

means for successively displaying objects at random locations against the background on the computer screen in a pattern to stimulate the eye muscles of the user to move the eyes to the successive random locations in the pattern to exercise the eyes for a certain time interval;

means for removing the displayed objects from the screen;

means for requesting a response to identifying the objects in the successive random locations corresponding to the objects successively displayed on the screen within a first time period; and means for sensing and recording a user response entered within said first time period.

14. An apparatus for progressively exercising the eye muscles of a user, comprising:

means for providing a plurality of choices of screen backgrounds of progressive difficulty such that varying levels of eye concentration will be required for the eyes to perceive an object displayed against;

means for providing a plurality of choices of different objects to be projected against the background on the screen in the exercise;

means for providing a plurality of choices of the length of time the objects will be displayed;

means for sensing and displaying the user's choice of a background on the screen corresponding to that chosen from said plurality of backgrounds;

means for sensing and sequentially displaying objects corresponding to those chosen from said plurality of choices of different objects in random locations on the screen in a pattern to require the eyes to concentrate to find the objects against the background and stimulate the eye muscles of the user to move the eyes to the random locations in a manner to exercise the eyes for a time interval corresponding to that chosen from said lengths of time the objects will be displayed;

means for removing the displayed objects from the screen;

means for requesting a user response identifying the objects displayed on the screen after each display;

means for sensing and recording the user response identifying each object displayed;

means for comparing the user response identifying each object to each object displayed on the screen; and means for assigning a quantitative value to each user response correctly identifying objects displayed depending upon the background, different objects and length of time chosen by the user.

15. A user interactive method of exercising the eye muscles, utilizing a computer connected to a computer display terminal having a screen, comprising:

placing a first-colored lens over the one eye and a second lens of a color different from the first-colored lens over the other eye;

displaying in the first stage of the exercise, a first object of the color of the first lens and a second object of the color of the second lens in a side-by-side relationship, partially overlapping each other on the screen, in a manner to stimulate the eye muscles to move the eyes to locate and view the overlapping objects as a single object;

moving said first and second objects away from each other in the same horizontal plane, in response to a first signal by the user while stimulating the eye muscles to continue to view the separating first and second objects as a single object;

halting movement of said first and second objects in response to a second signal initiated by the user, once the user can no longer reconcile the first and second objects into a single object;

displaying in a second stage of the exercise, said first object and said second object in a reverse side-by-side relationship to that initially displayed, partially overlapping over other, to stimulate the eye muscles to move the eyes of the user to view the overlapping objects as a single object moving said first and second objects away from each other in the same horizontal plane while the eye muscles continue to stimulate the eyes to view said first and second objects as a single object, in response to a third signal initiated by user; and halting the movement of said first and second objects, in response to a fourth signal by the user, once the user can no longer reconcile the two objects into a single object whereby the exercise will function to stimulate the eye muscles to both converge and diverge the eyes of the user.

16. The method of claim 15, further comprising the steps of:

determining and recording the elapsed time of the exercises; and repeating said steps of displaying in a first stage of the exercise, to stimulate the eye muscles to move the eyes to view the overlapping objects as a single object, moving said first and second objects apart while the eyes continue to view the objects as a single object, halting movement of said objects by the user, displaying the objects in reverse order in a second stage of the exercise to stimulate the eye muscles to control the eyes to view the overlapping objects as a single object, moving said first and second objects apart, and halting movement of said first and second objects by the user until a pre-determined elapsed time has been reached.

17. The method of claim 16, wherein:

said pre-determined elapsed time in said repeating step is about three minutes.

18. The method of claim 15 or claim 16, further comprising the steps of:

measuring the horizontal distance traveled by the objects in the first stage and second stage of the exercise once their movement was halted;

determining a quantitative score based on the horizontal distance traveled by the objects in the first stage of the exercise and the second state of the exercise; assigning a code identifying the user to the quantitative score; and storing the score from the first stage and second stage of the exercise with the code in a memory.

19. The method of claim 18, further comprising the steps of:

displaying a number of personal data questions;

recording and storing any user responses to a number of personal data questions in the memory; and cross-referencing and storing the responses with said score from the first and second stages of the exercise and said code in a memory.

20. The method of claim 18, further comprising the step of:

providing a plurality of speed selections corresponding to varying speeds at which said first and second objects will move away from each other to provide a progressive level of stimulation of the eye muscles of the user to control the eyes to view the said first and second objects as a single object; and wherein said steps of moving said first and second objects away from each other are carried out at a speed corresponding to the speed selection that has been chosen from said plurality of selections corresponding to varying speeds.

21. The method of claim 20, wherein said step of:

determining a quantitative score is also based upon the speed selection that has been chosen.

22. The method of claim 20 wherein the first and second objects have additional elements therein such that the acceptance of images and muscular balance of the user's eyes can be determined by the appearance and alignment perceived by the user.

23. An apparatus for exercising the eye muscles of a user of a computer having a screen comprising:

supporting means for positioning a first-colored lens over the one eye and a second lens of a color different from the first colored lens over the other eye;

means for displaying in a first stage of the exercise, a first object of the color of the first lens and a second object of the color of the second lens in a side-by-side relationship, partially overlapping each other on the computer screen, in a manner to stimulate the eye muscles of the user to move the eyes to view said first and second objects as a single object;

means for moving said first and second objects away from each other in the same horizontal plane on the computer screen while stimulating the eye muscles continue to view said first and second objects as a single object, in response to a first exercise beginning signal by the user;

means for halting movement of said first and second objects in response to a second signal by the user, once the user can no longer reconcile the two objects into a single viewed object;

means for displaying, in a second stage of the exercise, the first object and the second object in a reverse side-by-side relationship to that initially displayed, partially overlapping each other, in a manner to stimulate the eye muscles of the user to move the eyes to view said first and second objects as a single object;

means for moving said first and second objects away from each other in the same horizontal plane while stimulating the eye muscles to continue to view said first and second objects as a single object, in response to a third exercise beginning signal by the user; and means for halting horizontal movement of said first and second objects in response to a fourth signal by the user, once the user can no longer reconcile the two objects into a single object.

24. An apparatus for progressively exercising the eye muscles of a user comprising:

supporting means for positioning a first-colored lens over the one eye and a second lens of a color different from the color of the first lens over the other eye;

means for providing a plurality of selections corresponding to varying speeds at which the exercise will proceed;

means for selecting and displaying in a first stage of the exercise, a first object of the color of the first lens and a second object of the color of the second lens in a side-by-side relationship, partially overlapping each other on the computer screen, in a manner to stimulate the eye muscles of the user to move the eyes to view said first and second objects as a single object;

means for moving said first and second objects away from each other in the same horizontal plane on the computer screen while stimulating the eye muscles to continue to view said first and second objects as a single object, in response to a first beginning signal by the user;

means for halting horizontal movement of said first and second objects away from each other in response to a second signal by the user, once the user can no longer reconcile the two objects into a single object;

means for displaying, in a second stage of the exercise, said first object and said second object in a reverse side-by-side relationship to that initially displayed, partially overlapping each other, in a manner to stimulate the eye muscles of the user to move the eyes to view said first and second objects as a single object;

means for moving said first and second objects away from each other in the same horizontal plane, in response to a beginning third signal by the user; and means for halting movement of said first and second objects, in response to a fourth signal by the user, once the user can no longer reconcile viewing said first and second objects into a single object.

25. A user interactive method of exercising the eye muscles of a user that control focusing of the eyes, utilizing a computer connected to a computer display terminal having a screen, comprising the steps of:

displaying text on the screen for a first predetermined time interval to stimulate the eye muscles of the user to focus the eyes on the text on the screen;

removing the text from the screen;

directing the user to stimulate the eye muscles to focus the eyes on an object away from the screen located at a distance sufficient to cause the user to refocus this eyes for a second pre-determined time interval; and providing an audio signal at the end of the second pre-determined time interval to direct the user to again view the screen to stimulate the eye muscles to refocus the eyes on the text on the screen.

26. The method of claim 25, comprising the steps of:

determining and recording the elapsed time the user is engaged in the exercise;

determining and recording the number of screens of text displayed; and repeating said steps of displaying text, removing the text, directing the user to stimulate the eye muscles and providing an audio signal until the elapsed time reaches a certain first limit or said number of screens displayed reaches a second limit.

27. The method of claim 26, wherein:

said first limit is three minutes and said second limit is four.

28. The method of claim 25 wherein the second distance is at least ten feet.

29. An apparatus for exercising the eye muscles of a user that control focusing of the eyes, comprising;

means for displaying text on the screen of a computer for a first pre-determined time interval to stimulate the eye muscles of the eyes of a user to move the eye to focus on the text on the screen;

timed programmed means for removing the text from the screen;

programmed means for directing the user to look away from the screen for a second programmed pre-determined time interval and to focus the eyes on an object at a second distance sufficient to cause the eye muscles to stimulate the eyes to refocus on the distant object;

means for providing an audio signal to direct the user to again view the text on the screen and to stimulate the eye muscles of the user to refocus the eyes on the text on the screen.

30. A user interactive method of exercising the eye muscles, utilizing a computer connected to a computer display terminal having a screen, comprising the steps of:

displaying an object at a first random location on the background of the screen for a certain time interval to stimulate the eye muscles of the user to move the eyes to said first random location;

removing the displayed object from the screen;

requesting a response corresponding to the object displayed on the screen within a first time period;

sensing any user response within the first time period identifying the objects on the screen;

recording any response entered within the first time period;

placing a first-colored lens over one eye and a second lens of a color different from the first colored lens over the other eye;

displaying in a first stage of the exercise, a first object of the color of the first lens and a second object of the color of the second lens in a side-by-side relationship, partially overlapping each other on the computer screen, to simulate the eye muscles of the user to move the eyes to locate and view said first and second objects as one object:

moving said first and second objects away from each other in the same horizontal plane in response to a first signal initiated by the user while the eye muscles continue to be stimulated to enable the eyes to view the separating first and second objects as a single object;

halting the movement of said first and second objects in response to a second signal initiated by the user, once the user can no longer reconcile the said first and second objects into a single object;

displaying, in a second stage of the exercise, said first object said first second object in a reverse side-by-side relationship to that as initially displayed, such that said objects partially overlap each other, so that they appear as one object to the user to stimulate the eye muscles of the user to move the eyes to view said first and second objects as a single object;

moving said first and second objects away from each other in the same horizontal plane while the eyes are directed to the separating red and green objects on the screen, in response to a third signal initiated by the user;

halting movement of said first and second object on the screen, in response to a fourth signal by the user, once the user can no longer reconcile the two objects into a single object;

displaying text on the screen for a first pre-determined time interval to stimulate the eye muscles of the user to focus the eyes on the text on the screen;

removing the text from the screen;

directing the user to look away from the screen for a second pre-determined time interval;

directing the user to stimulate the eye muscles to focus the eyes on an object at a second distance away from the screen sufficient to cause the user to refocus his eyes for a second pre-determined time interval; and providing an audio signal at the end of the second pre-determined time interval to direct the user to again view the screen to stimulate the muscles of the eyes of the user to refocus the eyes on the text on the screen.

31. An interactive progressive method of exercising the eye muscles of a user of a computer connected to a computer display terminal having a screen, comprising the steps of:

providing a plurality of choices of background on the screen of progressive difficulty such that require varying levels of eye concentration, for the eyes to perceive an object displayed against the background;

providing a plurality of choices of a given number of different objects to be projected against the background on the screen in the exercise;

providing a plurality of choices of the length of time the objects will be displayed;

selecting a background, a given number of different objects, and length of time the objects are to be displayed from the pluralities of choices;

displaying a background on the screen corresponding to that selected from said plurality of background choices;

displaying on the screen one of a number of objects corresponding to that selected from said given number of different objects and for a length of time corresponding to that selected from said plurality of choices of the length of time the object will be displayed to require the eyes to concentrate to find the object against the background and to stimulate the eye muscles of the user to move the eyes to the location of the object on the screen;

removing the displayed object from the screen;

requesting a response corresponding to the object displayed on the screen within a first time period;

sensing any user response identifying the object perceived on the screen;

recording any identifying response to the user entered within the first time period;

comparing the identified object of the user sensed in the user response to the object displayed;

placing a first-colored lens over one eye and a second lens of a color different from the first-colored lens over the other eye;

displaying in a first stage of the exercise, a first object of the color of the first lens and a second object of the color of the second lens in a side-by-side relationship, partially overlapping each other on the computer screen, so that they appear as one object to the user to stimulate the eye muscles of the user to move the eyes to locate and view the overlapping objects as a single object;

providing a plurality of choices of speeds at which said first and second objects can be moved away from each other in the same horizontal plane;

selecting a speed from said plurality of choices of speed;

moving aid first and second objects away from each other in the same horizontal plane at a speed corresponding to the speed selected in said selecting stop, in response to a first signal initiated by the user while stimulating the eyes to continue to view the separating first and second objects as a single object;

halting movement of said first and second objects, in response to a second signal initiated by the user once the user can no longer reconcile said first and second objects into a single object;

displaying on the screen, in a second stage of the exercise, the first and the second object in a reverse side-by-side relationship to that initially displayed, partially overlapping each other, to stimulate the eye muscles of the user to move the eyes to locate and view said first and second objects as a single object;

moving said first and second objects away from each other in the same horizontal plane at a speed corresponding to the speed selected in said selecting step, in response to a third signal by the user while the eye muscles continue to view the object as a single object;

halting movement of said first and second objects in response to a fourth signal by the user, once the user can no longer reconcile the two objects into a single object;

displaying text on the screen for a first predetermined time interval to stimulate the eye muscles of the user to focus the eyes on the text on the screen;

removing the text from the screen;

directing the user to stimulate the eye muscles of the user to focus his eyes on an object at a second distance away from the screen sufficient to cause the user to refocus his eyes for a second pre-determined time interval;

providing an audio signal at the end of the second pre-determined time interval to direct the user to again view the screen to stimulate the muscles of the eyes of the user to refocus his eyes on the screen.

32. The method of claim 2, 3 or 8 wherein if said step of sensing any user response senses a response within a time period less than the first time period, the next object is then immediately thereafter displayed on the screen.

33. An interactive progressive method of exercising the eye muscles of a user of a computer connected to a computer display terminal having a screen, comprising the steps of;

providing a plurality of choices of background on the screen of progressive difficulty such that require varying levels of eye concentration of progressive difficulty for the eyes to perceive an object displayed against the background;

providing a plurality of choices of a given number of different objects to be projected against the background on the screen in the exercise;

providing a plurality of choices of the length of time the objects will be displayed;

selecting a background, a given number of different objects, and lengths of time the objects are to be displayed from the pluralities of choices;

displaying a background on the screen corresponding to that selected from said plurality of background choices;

displaying on the screen one of a number of objects corresponding to that selected from said given number of different objects and for a length of time corresponding to that selected from said plurality of choices of the length of time the object will be displayed to require the eyes to concentrate to find the object against the background stimulate the eye muscles of the user to move the eyes to the location of the object on the screen;

removing the displayed object from the screen;

requesting a response corresponding to the object displayed on the screen within a first time period;

sensing any user response identifying the object perceived on the screen;

recording any identifying response of the user entered within the first time period;

comparing the identified object of the user sensed in the user response to the object displayed;

placing a first-colored lens over one eye and a second lens of a color different from the first-colored lens over the other eye;

displaying in a first stage of the exercise, a first object of the color of the first lens and a second object of the color of the second lens in a side-by-side relationship, partially overlapping each other on the computer screen, so that they appear as one object to the user to stimulate the eye muscles of the user to move the eyes to locate and view the overlapping objects as a single object;

providing a plurality of choices of speeds at which said first and second objects can be moved away from each other in the same horizontal plane;

selecting a speed from said plurality of choices of speed;

moving said first and second objects away from each other in the same horizontal plane at a speed corresponding to the speed selected in said selecting step, in response to a first signal initiated by the user while stimulating the eyes to continue to view the separating first and second objects as a single object;

halting movement of said first and second objects, in response to a second signal initiated by the user once the user can no longer reconcile said first and second objects into a single object;

displaying on the screen, in a second stage of the exercise, the first and the second object in a reverse side-by-side relationship to that initially displayed, partially overlapping each other, to stimulate the eye muscles of the user to move the eyes to locate and view said first and second objects as a single object;

moving said first and second objects away from each other in the same horizontal plane at a speed corresponding to the speed selected in said selecting step in response to a third signal by the user while the eye muscles continue to view the object as a single object; and halting movement of said first and second objects in response to a fourth signal by the user, once the user can no longer reconcile the two objects into a single object.

34. The method of claims 15 or 33 wherein the first and second objects have additional elements therein such that the acceptable of images and muscular balance of the user's eyes can be determined by the appearance and alignment perceived by the user.

* * * * *